United States Patent
Fäcke et al.

(10) Patent No.: US 9,057,946 B2
(45) Date of Patent: Jun. 16, 2015

(54) DIFUNCTIONAL (METH)ACRYLATE WRITING MONOMERS

(75) Inventors: Thomas Fäcke, Leverkusen (DE); Friedrich-Karl Bruder, Krefeld (DE); Thomas Rölle, Leverkusen (DE); Marc-Stephan Weiser, Leverkusen (DE); Dennis Hönel, Zülpich-Wichterich (DE); Horst Berneth, Leverkusen (DE)

(73) Assignee: Bayer Intellectual Property GmbH, Monheim (DE)

( * ) Notice: Subject to any disclaimer, the term of this patent is extended or adjusted under 35 U.S.C. 154(b) by 132 days.

(21) Appl. No.: 13/814,725

(22) PCT Filed: Aug. 10, 2011

(86) PCT No.: PCT/EP2011/063785
§ 371 (c)(1),
(2), (4) Date: Jun. 11, 2013

(87) PCT Pub. No.: WO2012/020061
PCT Pub. Date: Feb. 16, 2012

(65) Prior Publication Data
US 2013/0252140 A1    Sep. 26, 2013

(30) Foreign Application Priority Data

Aug. 11, 2010  (EP) .................................... 10172536

(51) Int. Cl.
*G03H 1/02*    (2006.01)
*G03C 1/73*    (2006.01)
(Continued)

(52) U.S. Cl.
CPC ............... *G03C 1/733* (2013.01); *G11B 7/245* (2013.01); *G03H 2001/0264* (2013.01);
(Continued)

(58) Field of Classification Search
CPC .. G11B 7/245; G11B 7/24044; C08G 18/792; C08G 18/485; C08G 18/4825; C08G 18/4854; C08G 18/7831; C08G 18/44; C08G 18/4277; C08G 18/10; C08G 18/7837; C08G 18/7887; C08G 18/4238; G03F 7/001; G03F 7/0046; G03F 7/035

See application file for complete search history.

(56) References Cited

U.S. PATENT DOCUMENTS 5,260,149 A * 11/1993 Monroe et al. ................ 430/1
8,053,147 B2   11/2011 Stoeckel et al.
(Continued)

FOREIGN PATENT DOCUMENTS

EP     1627867 A1    2/2006
JP     02-150410  *  6/1990
(Continued)

OTHER PUBLICATIONS

International Search Report for PCT/EP2011/063785 Mailed Nov. 10, 2011.

*Primary Examiner* — Martin Angebranndt
(74) *Attorney, Agent, or Firm* — Drinker Biddle & Reath LLP

(57) ABSTRACT

The invention relates to compounds, of formula (I) in which X is $CH_3$ or hydrogen, Z is a linear or branched C2 to C4 alkyl radical, R is a linear or branched, optionally heteroatom-substituted aliphatic, aromatic or araliphatic radical, Y in each occurrence is independently hydrogen, methyl, ethyl, propyl, n-butyl, tert-butyl, chlorine, bromine, iodine, methylthio, phenyl or phenylthio, n is from 0 to 4 and m is from 0 to 5. The invention further relates to the use of such a compound as writing monomer in a photopolymer formulation. In addition, a photopolymer formulation comprising as least a polyisocyanate component, a polyol component, a photoinitiator and a compound of formula (I) as writing monomer, and also the use of the photopolymer formulation for producing holographic media, are likewise subjects of the invention.

6 Claims, 1 Drawing Sheet

(51) Int. Cl.
*G11B 7/245* (2006.01)
*G03H 1/30* (2006.01)
*G11B 7/24044* (2013.01)
*G03F 7/004* (2006.01)
*C07C 323/12* (2006.01)
*C09D 175/04* (2006.01)
*G03F 7/00* (2006.01)
*G03F 7/027* (2006.01)

(52) U.S. Cl.
CPC ............ *G03H 2260/12* (2013.01); *G03H 1/30* (2013.01); *G11B 7/24044* (2013.01); *G03F 7/0046* (2013.01); *C07C 323/12* (2013.01); *C09D 175/04* (2013.01); *G03F 7/001* (2013.01); *G03F 7/027* (2013.01)

(56) References Cited

U.S. PATENT DOCUMENTS

| | | | |
|---|---|---|---|
| 2002/0142227 A1* | 10/2002 | Dhar et al. | 430/1 |
| 2008/0312403 A1* | 12/2008 | Stockel et al. | 528/59 |
| 2009/0131550 A1* | 5/2009 | Arai et al. | 522/174 |
| 2009/0185470 A1 | 7/2009 | Stoeckel et al. | |
| 2011/0236803 A1* | 9/2011 | Weiser et al. | 430/2 |

FOREIGN PATENT DOCUMENTS

| | | | |
|---|---|---|---|
| WO | 2008120573 A1 | | 10/2008 |
| WO | 2008125229 A1 | | 10/2008 |
| WO | 2012-003136 | * | 1/2012 |

* cited by examiner

DIFUNCTIONAL (METH)ACRYLATE WRITING MONOMERS

CROSS REFERENCE TO RELATED APPLICATIONS

This application is a §371 National Stage Application of PCT/EP2011/063785, filed Aug. 10, 2011, which claims priority to European Application No. 10172536.4, filed Aug. 11, 2010.

BACKGROUND OF THE INVENTION

1. Field of the Invention

The invention relates to a compound particularly useful as a writing monomer in photopolymer formulations. The invention further relates to a photopolymer formulation comprising at least a polyol component, a polyisocyanate component, a writing monomer and a photoinitiator and also to the use of the photopolymer formulation for producing holographic media.

2. Description of Related Art

The uses for photopolymer formulations are decisively determined by the refractive index contrast Δn produced in the photopolymer by holographic exposure. In holographic exposure, the interference field of signal light beam and reference light beam (in the simplest case, that of two plane waves) is mapped into a refractive index grating by the local photopolymerization of, for example, high refractive index acrylates at loci of high intensity in the interference field. The refractive index grating in the photopolymer (the hologram) contains all the information of the signal light beam. Illuminating the hologram with the reference light beam only will then reconstruct the signal. The strength of the signal thus reconstructed relative to the strength of the incident reference light is called diffraction efficiency, DE in what follows.

In the simplest case of a hologram resulting from the superposition of two plane waves, the DE is the ratio of the intensity of the light diffracted on reconstruction to the sum total of the intensities of the incident reference light and the diffracted light. The higher the DE, the greater the efficiency of a hologram with regard to the amount of reference light needed to visualize the signal with a fixed brightness.

High refractive index acrylates are capable of producing refractive index gratings of high amplitude between regions of low refractive index and regions of high refractive index and hence of producing holograms of high DE and high Δn in photopolymer formulations. It must be noted that DE is dependent on the product of Δn and the photopolymer layer thickness d. The width of the angular range in which the hologram is visualized (reconstructed) on monochromatic illumination, for example, is solely dependent on the layer thickness d.

When the hologram is illuminated with white light, for example, the width of the spectral range which can contribute to reconstructing the hologram is likewise only dependent on the layer thickness d. The relationship is that the smaller the d, the greater the particular acceptance widths. Therefore, to produce bright and easily visible holograms, it is generally desirable to seek a high Δn and a low thickness d while maximizing DE. That is, increasing Δn increases the latitude to engineer the layer thickness d without loss of DE for bright holograms. Therefore, the optimization of Δn is of outstanding importance in the optimization of photopolymer formulations (P. Hariharan, Optical Holography, 2nd Edition, Cambridge University Press, 1996).

WO 2008/125229 A1 discloses photopolymer formulations comprising mono- and difunctional writing monomers of high molecular weight. The media comprising these formulations make it possible to write reflection holograms that are very useful for data storage for example. However, producing and processing the formulations presents problems: the writing monomers comprised therein have a high viscosity and/or high $T_G$ values ($T_G$=glass transition temperature). This makes it difficult to achieve a uniform distribution of the writing monomers in the photopolymer formulation and a medium produced therefrom. In addition, when the known formulations are used, writing monomer agglomerates can form in the polymer matrix and appreciably compromise the quality of the media and/or of the holograms written therein. In such cases, the holographic materials become hazy.

WO 2008/125199 describes trifunctional urethane acrylate writing monomers and photopolymer formulations comprising same. They make it possible to achieve a particularly high refractive index contrast when the formulations additionally contain specific fluorourethanes. Such fluorourethanes and their use in photopolymer formulations are described for example in the as yet unpublished European application of application number are EP 09013770.4.

In principle, with these formulations, the refractive index contrast increases with the fluorourethane content. However, as the fluorourethane content increases, the optical quality becomes impaired by haze.

Transmission holograms are a particular form of holograms in that the reference beam and the object beam irradiate the holographic medium from the same side to produce the holograms. Transmission holograms have various applications. Light guidance is to be mentioned in particular here as a diffractive optical element. Such optical element can be used in demanding applications such as spectroscopy or astronomy. They are similarly suitable for use in electronic 3D displays.

Owing to the geometry of the object and signal beams which are made to interfere, the grating spacing in transmission holograms is large compared with reflection holograms. Depending on the wavelength, the grating spacing can be between 500-1000 nm. Since the mechanism of hologram formation in the photopolymer formulations is based on the diffusion of the writing monomers, it is difficult to develop writing monomers that are able to diffuse sufficiently far in the case of the large grating spacing customary for transmission holograms. Yet this is a prerequisite to achieve a high refractive index contrast (Δn). The photopolymers known from the area of reflection holograms are frequently not suitable for this in that they do not lead to a sufficiently high refractive index contrast.

SUMMARY

The present invention accordingly had for its object to provide a compound useful as writing monomer for production of holographic media for transmission holograms of high refractive index contrast (Δn). In addition, the compound should preferably also not contribute to any impairment of the optical quality of the holographic media by haze for example.

This object is achieved by a compound of formula (I)

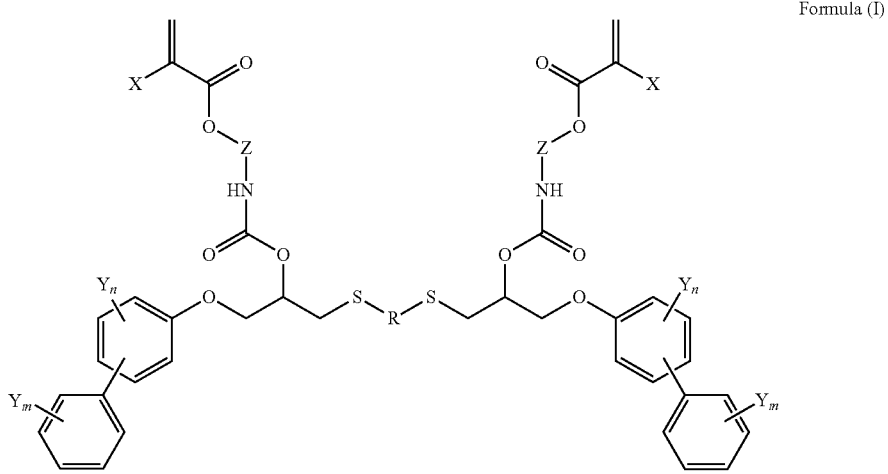

Formula (I)

where
X is CH₃ or hydrogen,
Z is a linear or branched C2 to C4 alkyl radical,
R is a linear or branched, optionally heteroatom-substituted aliphatic, aromatic or araliphatic radical,
Y in each occurrence is independently hydrogen, methyl, ethyl, propyl, n-butyl, tert-butyl, chlorine, bromine, iodine, methylthio, phenyl or phenylthio,
n is from 0 to 4 and
m is from 0 to 5.

DETAILED DESCRIPTION OF A PREFERRED EMBODIMENT

Figure 1:
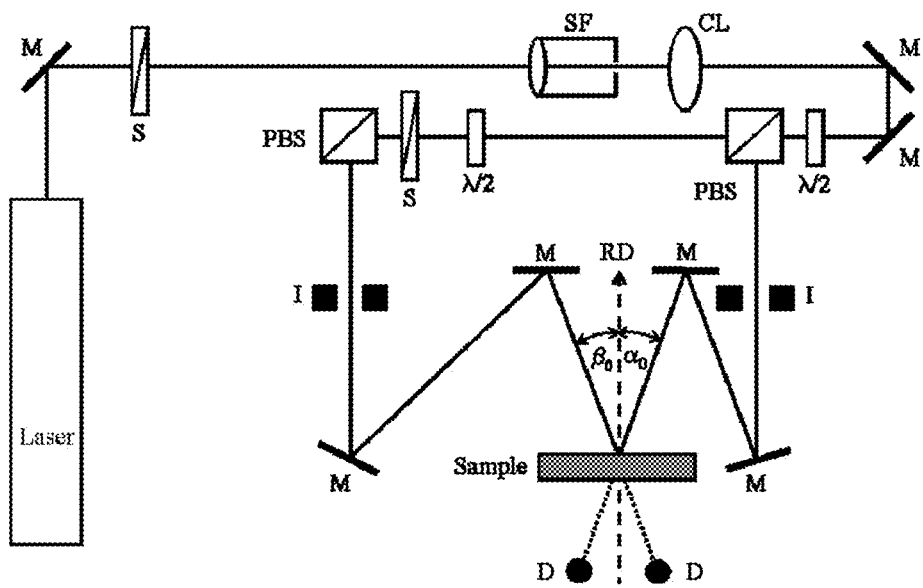
FIGS. 1-2 represent embodiments as described herein.

The inventors found that the compounds according to the invention can be used to obtain photopolymer formulations which in turn can be used to obtain holographic media especially for recording transmission holograms. These media not only have a high optical quality but also provide a high refractive index contrast ($\Delta n$) in the case of transmission holograms in particular.

EP 1 627 867 A1 discloses compounds which are structurally similar to formula (I) which, when used as writing monomers for production of transmission holograms, do not provide the high refractive index contrast to be achieved according to the present invention. This is evidenced by a comparative example in the experimental part of the application.

In a first preferred embodiment, R is a linearly or branched aliphatic, aromatic or araliphatic radical of 2 to 22 carbon atoms, which preferably is substituted with one or more oxygen, nitrogen and/or sulphur atoms. It is further preferred when R has 2 to 16 carbon atoms, 0 to 4 oxygen atoms, 0 to 1 nitrogen atoms and 0 to 1 sulphur atoms. In these cases, a particularly high refractive index contrast can be realized.

It is also possible for R to comprise at least one functional group selected from the group ether (—O—), thioether (—S—), ester (—O—CO), urethane (NH—CO). In this case, R may thus more particularly comprise linear or branched, optionally heteroatom-substituted aliphatic, aromatic or araliphatic ethers, thioethers, esters or urethanes, in which case these compounds can in turn be preferably aliphatic in nature.

It is very particularly preferable for R to be $(CH_2)_l$ with l=2 to 10, $(CH_2CH_2\text{—}O)_m\text{—}CH_2\text{—}CH_2$ with m=1 or 2, $CH(CH_3)\text{—}CH(CH_3)$, $CH_2\text{—}CO\text{—}OCH_2\text{—}CH_2\text{—}O\text{—}CO\text{—}CH_2$, phenylene-S-phenylene and/or $CH_2\text{—}CH(CH_2\text{—}O\text{—}CO\text{—}NH\text{-phenylene-5-phenyl})$.

Preference is also given to compounds of formula (I) in which X is hydrogen.

The substituents Y may each be independently H, methyl, phenyl, methylthio or phenylthio and preferably hydrogen.

In a further preferred embodiment, the compound of formula (I) may have n≥1 and ≤4 and/or m≥1 and ≤5. It is further preferable for m+n to be <4.

It is further advantageous for the Z groups each to be $(CH_2)_i$ with i≥2 and ≤4 or a —CH2-CH(CH₃)— radical. It is very particularly preferable for the Z's to be —CH₂—CH₂-radicals.

The di(meth)acrylates according to the invention are obtainable in a two-stage process. A monofunctional biphenyl glycidyl ether is initially reacted with a difunctional thiol in a first step of this process. The addition takes place strictly onto the sterically less bulky side of the oxirane, so that secondary alcohols are always formed. Subsequently, the alcohol formed is added twice onto 2-isocyanatoalkyl(meth)acrylate to form the di(meth)acrylate of the invention. This process is depicted by way of example in the following two-stage reaction scheme:

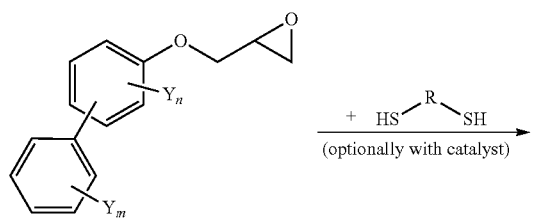

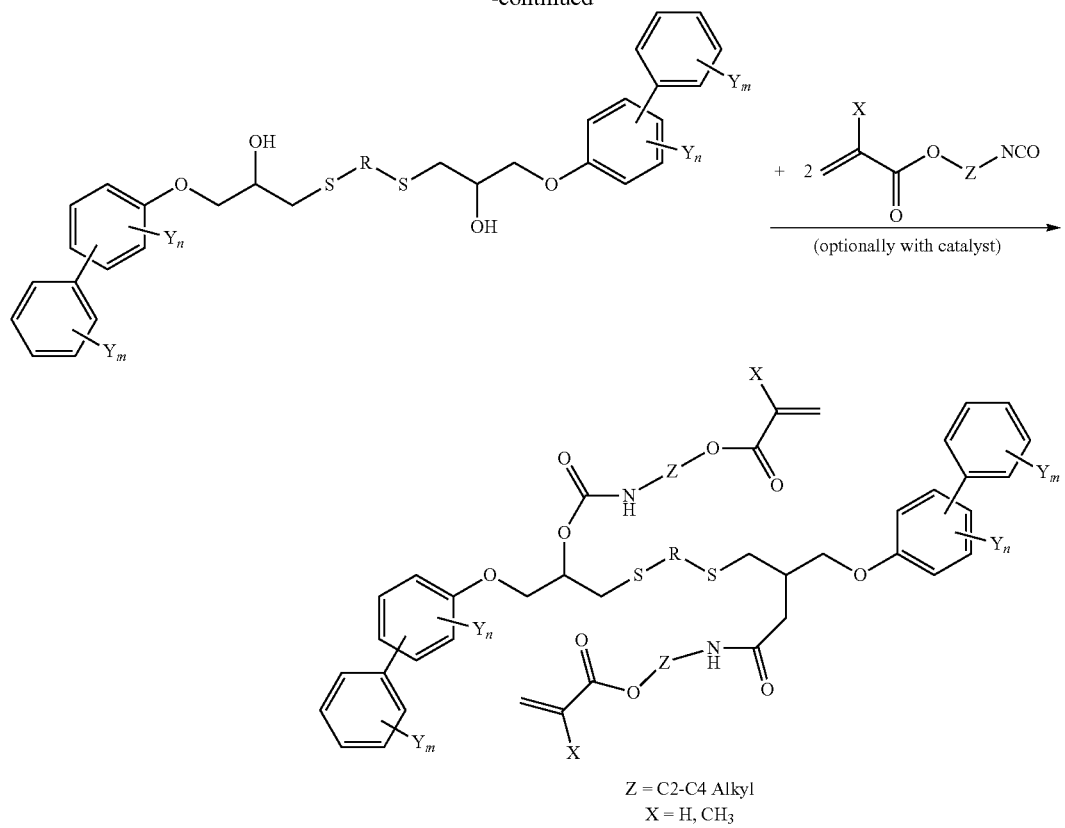

Z = C2-C4 Alkyl
X = H, CH₃

The compounds according to the invention can be prepared using monofunctional biphenyl glycidyl ethers. These are obtainable from the corresponding phenylphenols e.g. by reaction with epichlorohydrin or epibromohydrin in the presence of bases to neutralize the resulting hydrochloric or, respectively, hydrobromic acid. Potassium carbonate is useful as a base here for example.

Suitable phenylphenols are ortho-phenylphenol, meta-phenylphenol and para-phenylphenol. It is also possible to use substituted ortho-phenylphenol, substituted meta-phenylphenol and substituted para-phenylphenol respectively. The phenylphenols can also be substituted with two or more substituents, in which case identical and also different substituents on one of the two phenyl rings or on both rings of the phenylphenol are possible. Possible substituents Y are short-chain alkyl radicals such as methyl, ethyl, propyl, n-butyl, t-butyl, and/or halogen atoms such as chlorine, bromine, iodine and also thioethers such as methylthio, phenylthio, and/or aromatic substituents such as phenyl.

Preferred substituents Y are methyl, phenyl, methylthio and/or phenylthio. It is particularly preferable when the total number of identical or different substituents distributed over the two rings is not more than three (m+n≤4).

It is further preferable to have monosubstituted and unsubstituted phenylphenols with Y=H, methyl, phenyl, methylthio and phenylthio. ortho-Phenylphenol and meta-phenylphenol are very particularly preferred.

The di(meth)acrylates according to the invention can be prepared using aliphatic, aromatic and/or araliphatic both linear and/or branched, difunctional thiols with 1-40 carbon and also optionally in addition oxygen, nitrogen, phosphorus, sulphur, chlorine, bromine and iodine atoms.

Preferred difunctional thiols contain in total 4-22 carbon, oxygen, nitrogen or sulphur atoms, and particularly preferred ones contain 2-16 carbon, 0-4 oxygen, 0-1 nitrogen atom and 0-3 sulphur atoms.

General preference is given to difunctional thiols containing one or more ether (—O—), thioether (—S—), ester (—O—CO), thioester (—O—CS—), dithioester (—S—CS—), urethane (NH—CO), thiourethanes (NH—CS), ortho-, meta- and para phenylene (-phenyl-), methylthio (MeS—), phenylthio (PhS—), phenyl (Ph-), methyl (CH₃—) and/or napthyl (C₁₀H₇—) groups.

Particularly preferred dithiols are such compounds containing one or more ether (—O—), thioether (—S—), ester (—O—CO), urethane (NH—CO), ortho-, meta- and para phenylene (-phenyl-), methylthio (MeS—) and/or phenylthio (PhS—) groups.

It is possible to use aliphatic unbranched dithiols such as 1,2-ethanedithiol, 1,3-propanedithiol, 1,4-butanedithiol, 1,5-pentanedithiol, 1,6-hexanedithiol, 1,7-heptanedithiol, 1,8-octanedithiol, 1,9-nonanedithiol, 1,10-decanedithiol, 1,11-undecanedithiol, 1,12-dodecanedithiol, 1,16-hexadecanedithiol, 1,18-octadecanedithiol, as well as branched dithiols such as, for example, 1,2-propanedithiol, 1,2-butanedithiol, 2,3-butanedithiol, 1,3-butanedithiol, the isomeric pentanedithiols (e.g. 2,3-pentaneditiol), hexanedithiols (e.g: 3,4-hexanedithiols), heptaneditiol, octanedithiols (e.g. 2-ethyl-1,3-hexanedithiol), nonanedithiols, decanedithiols, undecanedithiols, dodecanedithiols and hexadodecanedithiol, octadecanedithiols and also cycloaliphatic dithiols such as, for example, 2-methyl-4-(1-sulphanylpropan-2-yl)cyclohexanethiol.

Ether- and thioether-containing dithiols, for example 2,2'-oxydiethanethiol, 2,2'-sulphanediyldiethanethiol (DMDES), 1,2-bis(2-mercaptoethoxy)ethane, 2,2'-[oxybis(ethane-2,1-diyloxy)]diethanethiol, as well as dithiols containing ester groups such as, for example, ethylene glycol dimercaptoacetate, ethylene glycol dimercaptoproprionate, propylene glycol dimercaptoacetate, propylene glycol dimercaptoproprionate, butylene glycol dimercaptoacetate, butylene glycol dimercaptoproprionate, hexylene glycol dimercaptoacetate, hexylene glycol dimercaptoproprionate as well as ether- and ester-containing dithiols such as, for example, diethylene glycol dimercaptoacetate, diethylene glycol dimercaptoproprionate can likewise be used.

Furthermore, aromatic dithiols such as, for example, 1,2-benzenedithiol, 1,3-benzenedithiol, 1,4-benzenedithiol, 4,4'-sulphanediyldibenzenethiol (4,4'-thiobisbenzenethiol) and araliphatic dithiols such as, for example, 1,4-benzenedimethanethiol, 1,3-benzenedimethanethiol, 1,2-benzenedimethanethiol and 2-(mercaptomethyl)phenylmethanethiol, 3-(mercaptomethyl)phenylmethanethiol and/or 4-(mercaptomethyl)-phenylmethanethiol are also suitable.

Finally, it is also possible to use dithiols bearing alcohol groups such as, for example, 2,3-disulphanylpropan-1-ol and/or 1,4-disulphanylbutane-2,3-diol. With these, it is not just the alcohols formed by the thiol-oxirane addition which can be urethanized in the second stage of the reaction, but also the alcohol groups already present in the dithiols bearing alcohol groups.

It is possible in this connection for the alcohol group to be urethanized before the addition of the thiol groups onto the oxirane. Alternatively, the urethanization can take place after the addition reaction. A particular factor in this connection is to be able to exploit the differing reactivity of primary versus secondary or tertiary alcohols. For instance, the primary alcohol group of 2,3-disulphanylpropan-1-ol can initially be selectively urethanized before or after the thiol-oxirane reaction and then the secondary alcohol groups from the thiol-oxirane reaction can be reacted at higher temperatures and/or higher catalyst quantity. This approach makes it possible to react either all the alcohol groups with an isocyanato(meth)acrylate or the primary alcohol group with a monoisocyanate and the secondary alcohol groups with isocyanato(meth)acrylate.

Suitable monoisocyanates for such a urethanization are phenyl isocyanate, 2-, 3- and 4-tolyl isocyanate, the isomeric 2-, 3- and 4-biphenyl isocyanate, 3,4-dichlorophenyl isocyanate, the isomeric 2- and 3-napthylisocyanate, the isomeric 2-, 3- and 4-methylthiophenyl isocyanate and the isomeric 2-, 3- and 4-phenylthiophenyl isocyanate. Preference is given to methylthiophenyl isocyanate and phenylthiophenyl isocyanate.

The thiol-oxirane reaction can be carried out without catalyst, although this will lead to very long reaction times and/or low conversions in some cases. When no catalyst is used, it is frequently necessary to employ high temperatures which can then lead to an unwelcome increase in the colour number of the products.

It is therefore advantageous in this connection to add a catalyst, typically in the amount of 0.02-1% by weight. This catalyst can be present in the reaction mixture from the start or else only be added during the reaction.

Various classes of substances can be used as catalysts: examples are Broensted acids such as phosphoric acid, phosphorous acid, sulphuric acid; Lewis acids such as zinc acetates, zinc cetylacetonates, titanium(IV) methoxide, tetrakis(dimethylamino)zirconium, Lewis bases such as 2-methylimidazoles, dimethylaminopyridine, borane-pyridine complex, tris(dimethylamino)borane, triphenylphosphine, tris(o-tolyl)phosphine, choline chlorides, tris(4-dimethyleneaminophenyl)phosphine, tris(4-methoxyphenyl)phosphine, 1,4,5,6-tetrahydropyrimidine, diazabicycloundecane (DABCO) and other amines, and ammonium or phosphonium salts, for example tetraethylammonium trifluoroacetate, tetrabutylphosphonium bromide, benzyltrimethylammonium bromide, benzyltrimethylammonium chloride, 1-butyl-1-methylpyrrolidinium bromides, 1-butyl-1-methylpyrrolidinium chlorides, tetrabutylphosphonium chloride and tetrabutylphosphonium bromide, tetraphenylphosphonium chloride and tetraphenylphosphonium bromide, triphenylbutylphosphonium chloride and triphenylbutylphosphonium bromide, triphenylethylphosphonium chloride and triphenylethylphosphonium bromide as well as tetrakis(dimethylamino)silane.

It is also possible to use imidazoles such as 1,2-dimethyl-3-propylimidazolium iodide, 1,3-dimethylimidazolium chloride, 1-butyl-2,3-dimethylimidazolium chloride, 1-butyl-3-methylimidazolium bromide, 1-butyl-3-methylimidazolium chloride, 1-butyl-3-methylimidazolium iodide, 1-ethyl-3-methylimidazolium bromide, 1-ethyl-3-methylimidazolium chloride, 1-ethyl-3-methylimidazolium iodide, 1-ethyl-3-methylimidazolium iodide, 1-hexyl-3-methylimidazolium bromide, 1-hexyl-3-methylimidazolium chloride, 1-methyl-3-n-octylimidazolium bromide, 1-methyl-3-n-octylimidazolium chloride, 1-methyl-3-propylimidazolium iodide.

Also useful are pyridines such as for example: 1-butyl-3-methylpyridinium bromide, 1-butyl-3-methylpyridinium chloride, 1-butyl-4-methylpyridinium bromide, 1-butyl-4-methylpyridinium chloride, 1-butylpyridinium bromide, 1-butylpyridinium chloride, 1-ethylpyridinium bromide, 1-ethylpyridinium chloride.

Preference is given to triphenylphosphine and 1-butyl-3-methylimidazolium bromide.

The reaction for thiol addition on the oxirane can be run at temperatures between 20° C. and 100° C. and typically at 60° C., depending on the activity, by initially charging the oxirane and the catalyst and then gradually adding the thiol dropwise. The thiol can likewise be initially charged and the oxirane then added dropwise.

To achieve speedy and complete reaction, the reaction temperature used is not more than 130° C., although higher temperatures are also possible, in which case however secondary reactions and undesirable formation of colour are observed. The reaction can be carried out in the absence of oxygen. But it is generally not necessary for oxygen to be absent. Typically, following the slightly to fairly vigorously exothermic reaction during the dropwise addition, temperatures of 70° C. to 90° C. are subsequently set to complete the reaction.

A small excess (not more than 10 mol %) of oxirane can be advantageous in order that the troublesome odour of unconverted thiol may be avoided. This is advantageous in the case of the low molecular weight volatile dithiols in particular.

The end of the reaction can be detected via $^1$H NMR spectroscopy (the oxirane gives characteristic resonances in the $^1$H NMR (400 MHz, CDCl$_3$): δ=2.6 (dd), 2.8 (dd), 3.2 (m)).

Solvents can be additionally added to police the viscosity of the reaction. This can be advantageous with aromatic and araliphatic dithiols in particular. Aliphatic dithiols, by contrast, can generally be reacted without solvent.

The alcohols are urethanized in the second reaction step.

The urethanization temperature is typically 20-180° C., preferably 40-120° C. and more preferably 50-100° C. A possible procedure for the urethanization is for the alcohol to be initially charged as product of the first stage and to be optionally admixed with a catalyst and then for the isocyanate to be added dropwise.

The reaction has ended when the NCO content has dropped to below 1% and preferably below 0.1% by weight. This NCO content can be determined via IR spectroscopy or by titration.

It is likewise possible to initially charge the isocyanate and then to add the alcohol dropwise. The preferred mode of addition is influenced in the specific case by the handling and hence the viscosity of the starting materials.

Useful catalysts for the urethanization include amines and also metal compounds of the metals tin, zinc, iron, bismuth, molybdenum, cobalt, calcium, magnesium and zirconium.

Preference is given to tin octoate, zinc octoate, dibutyltin dilaurate, dimethyltin dicarboxylate, iron(III) acetylacetonate, iron(II) chloride, zinc chloride, tetraalkylammonium hydroxides, alkali metal hydroxides, alkali metal alkoxides, alkali metal salts of long-chain fatty acids having 10 to 20 carbon atoms and optionally lateral OH groups, lead octoate or tertiary amines such as triethylamine, tributylamine, dimethylbenzylamine, dicyclohexylmethylamine, dimethylcyclohexylamine, N,N,N',N'-tetramethyldiaminodiethyl ether, bis(dimethylaminopropyl)urea, N-methylmorpholine, N-ethylmorpholine, N,N'-dimorpholinodiethyl ether (DM-DEE), N-cyclohexylmorpholine, N,N,N',N'-tetramethylethylenediamine, N,N,N',N'-tetramethylbutanediamine, N,N,N',N'-tetramethylhexane-1,6-diamine, pentamethyldiethylenetriamine, dimethylpiperazine, N-dimethylaminoethylpiperidine, 1,2-dimethylimidazole, N-hydroxypropylimidazole, 1-azabicyclo-(2,2,0)octane, 1,4-diazabicyclo-(2,2,2)-octane (Dabco) or alkanolamine compounds such as triethanolamine, triisopropanolamine, N-methyldiethanolamine, and N-ethyldiethanolamine, dimethylaminoethanol, 2-(N,N-dimethylaminoethoxy)ethanol or N-tris(dialkylaminoalkyl)hexahydrotriazines, e.g. N,N',N'-tris(dimethylaminopropyl)-s-hexahydrotriazine, diazabicyclononane, diazabicycloundecane, 1,1,3,3-tetramethylguanidine, 1,3,4,6,7,8-hexahydro-1-methyl-2H-pyrimido(1,2-a)pyrimidine.

Particularly preferred catalysts are dibutyltin dilaurate, dimethyltin dicarboxylate, iron(III) acetylacetonate, 1,4-diazabicyclo-[2.2.2]-octane, diazabicyclononane, diazabicycloundecane, 1,1,3,3-tetramethylguanidine, 1,3,4,6,7,8-hexahydro-1-methyl-2H-pyrimido(1,2-a)pyrimidine.

Air is typically passed through during the urethanization in order that unwanted polymerization may be avoided. Care must be taken that there is a sufficient presence of phenols such as, for example, p-methoxyphenol or ionol (2,6) with amounts between 0.001-0.1 weight percent being advantageous. Suitable free-radical stabilizers include inhibitors and antioxidants as described in "Methoden der organischen Chemie" (Houben-Weyl), 4th edition, volume XIV/1, pp. 433ff, Georg Thieme Verlag, Stuttgart 1961. Suitable classes of compounds are for example phenols such as, for example, 2,6-ditert-butyl-4-methylphenol, cresols, hydroquinones, benzyl alcohols such as, for example, benzhydrol, optionally even quinones such as, for example, 2,5-ditert-butylquinone, optionally even aromatic amines such as diisopropylamine or phenothiazine. Preferred free-radical stabilizers are 2,6-ditert-butyl-4-methylphenol, phenothiazine and benzhydrol.

The compounds according to the invention is obtained by reacting the two secondary alcohol groups formed by addition of the dithiol onto the monooxirane with an acrylate-containing isocyanate component, useful isocyanate components being particularly isocyanatoethyl acrylate or isocyanatoethyl methacrylate. A mixture of the two components can likewise be used.

Using a dithiol bearing alcohol groups in addition, these can likewise be reacted with an acrylate-containing isocyanate component containing higher functional acrylates. It is likewise possible to react such an additional alkyl group selectively, as described above, with monoisocyanates without acrylate function. In this case, a urethane group is inserted within the R group.

The invention further provides for the use of a compound according to formula (I) as writing monomer in a photopolymer formulation.

The invention further provides a photopolymer formulation comprising at least a polyisocyanate component a), a polyol component b), a photoinitiator c) and a writing monomer d), wherein the photopolymer formulation contains at least one compound according to formula (I) as writing monomer.

As polyisocyanate component a) there can be used any compounds known per se to a person skilled in the art, or mixtures thereof, which on average contain two or more NCO functions per molecule. These can be aromatic, araliphatic, aliphatic or cycloaliphatic based. Monoisocyanates and/or unsaturation-containing polyisocyanates can also be used, in minor amounts.

Suitable examples are butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate, the isomeric bis(4,4'-isocyanatocyclohexyl)methane and mixtures thereof having any desired isomer content, isocyanatomethyl-1,8-octane diisocyanate, 1,4-cyclohexylene diisocyanate, the isomeric cyclohexanedimethylene diisocyanates, 1,4-phenylene diisocyanate, 2,4- and/or 2,6-tolylene diisocyanate, 1,5-naphthylene diisocyanate, 2,4'- or 4,4'-diphenylmethane diisocyanate and/or triphenylmethane 4,4',4''-triisocyanate.

It is likewise possible to use derivatives of monomeric di- or triisocyanates having urethane, urea, carbodiimide, acylurea, isocyanurate, allophanate, biuret, oxadiazinetrione, uretdione and/or iminooxadiazinedione structures.

Preference is given to using polyisocyanates based on aliphatic and/or cycloaliphatic di- or triisocyanates.

It is particularly preferable for the polyisocyanates of component a) to comprise di- or oligomerized aliphatic and/or cycloaliphatic di- or triisocyanates.

Very particular preference is given to isocyanurates, uretdiones and/or iminooxadiazinediones based on HDI and also 1,8-diisocyanato-4-(isocyanatomethyl)octane or mixtures thereof.

Likewise useful as component a) are NCO-functional prepolymers having urethane, allophanate, biuret and/or amide groups. Prepolymers of component a) are obtained in a well-known conventional manner by reacting monomeric, oligomeric or polyisocyanates a1) with isocyanate-reactive compounds a2) in suitable stoichiometry in the presence or absence of catalysts and solvents.

Useful polyisocyanates a1) include all aliphatic, cycloaliphatic, aromatic or araliphatic di- and triisocyanates known per se to a person skilled in the art, it being immaterial whether they were obtained by phosgenation or by phosgene-free processes. In addition, it is also possible to use the well-known conventional higher molecular weight descendant products of monomeric di- and/or triisocyanates having a urethane, urea, carbodiimide, acylurea, isocyanurate, allophanate, biuret, oxadiazinetrione, uretdione or iminooxadiazinedione structure each individually or in any desired mixtures among each other.

Examples of suitable monomeric di- or triisocyanates useful as component a1) are butylene diisocyanate, hexamethylene diisocyanate (HDI), isophorone diisocyanate (IPDI), trimethylhexamethylene diisocyanate (TMDI), 1,8-diisocyanato-4-(isocyanatomethyl)octane, isocyanatomethyl-1,8-octane diisocyanate (TIN), 2,4- and/or 2,6-toluene diisocyanate.

The isocyanate-reactive compounds a2) for constructing the prepolymers are preferably OH-functional compounds. These are analogous to the OH-functional compounds described hereinbelow for component b).

The use of amines for prepolymer preparation is also possible. For example, ethylenediamine, diethylenetriamine, triethylenetetramine, propylenediamine, diaminocyclohexane, diaminobenzene, diaminobisphenyl, difunctional polyamines, such as, for example, the Jeffamine® amine-terminated polymers having number average molar masses of up to 10 000 g/mol and any desired mixtures thereof with one another are suitable.

For the preparation of prepolymers containing biuret groups, isocyanate is reacted in excess with amine, a biuret group forming. All oligomeric or polymeric, primary or secondary, difunctional amines of the abovementioned type are suitable as amines in this case for the reaction with the di-, tri- and polyisocyanates mentioned.

Preferred prepolymers are urethanes, allophanates or biurets obtained from aliphatic isocyanate-functional compounds and oligomeric or polymeric isocyanate-reactive compounds having number average molar masses of 200 to 10 000 g/mol; particular preference is given to urethanes, allophanates or biurets obtained from aliphatic isocyanate-functional compounds and oligomeric or polymeric polyols or polyamines having number average molar masses of 500 to 8500 g/mol. Very particular preference is given to allophanates formed from HDI or TMDI and difunctional polyetherpolyols having number average molar masses of 1000 to 8200 g/mol.

The prepolymers described above preferably have residual contents of free monomeric isocyanate of less than 1% by weight, particularly preferably less than 0.5% by weight, very particularly preferably less than 0.2% by weight.

In addition to the prepolymers described, the isocyanate component can of course contain further isocyanate components proportionately. Aromatic, araliphatic, aliphatic and cycloaliphatic di-, tri- or polyisocyanates are suitable for this purpose. It is also possible to use mixtures of such di-, tri- or polyisocyanates. Examples of suitable di-, tri- or polyisocyanates are butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate (TMDI), the isomeric bis(4,4'-isocyanatocyclohexyl)methanes and mixtures thereof having any desired isomer content, isocyanatomethyl-1,8-octane diisocyanate, 1,4-cyclohexylene diisocyanate, the isomeric cyclohexanedimethylene diisocyanates, 1,4-phenylene diisocyanate, 2,4- and/or 2,6-tolylene diisocyanate, 1,5-naphthylene diisocyanate, 2,4'- or 4,4'-diphenylmethane diisocyanate, triphenylmethane 4,4',4"-triisocyanate or derivatives thereof having a urethane, urea, carbodiimide, acylurea, isocyanurate, allophanate, biuret, oxadiazinetrione, uretdione or iminooxadiazinedione structure and mixtures thereof. Polyisocyanates based on oligomerized and/or derivatized diisocyanates which were freed from excess diisocyanate by suitable processes are preferred. The oligomeric isocyanurates, uretdiones and iminooxadiazinediones of HDI and mixtures thereof are particularly preferred.

It is optionally also possible for the isocyanate component a) proportionately to contain isocyanates, which are partially reacted with isocyanate-reactive ethylenically unsaturated compounds. α,β-Unsaturated carboxylic acid derivatives, such as acrylates, methacrylates, maleates, fumarates, maleimides, acrylamides, and vinyl ethers, propenyl ethers, allyl ethers and compounds which contain dicyclopentadienyl units and have at least one group reactive towards isocyanate are preferably used here as isocyanate-reactive ethylenically unsaturated compounds; these are particularly preferably acrylates and methacrylates having at least one isocyanate-reactive group. Suitable hydroxy-functional acrylates or methacrylates are, for example, compounds such as 2-hydroxyethyl(meth)acrylate, polyethylene oxide mono(meth)acrylates, polypropylene oxide mono(meth)acrylates, polyalkylene oxide mono(meth)acrylates, poly(ε-caprolactone) mono(meth)acrylates, such as, for example, Tone® M100 (Dow, USA), 2-hydroxypropyl(meth)acrylate, 4-hydroxybutyl(meth)acrylate, 3-hydroxy-2,2-dimethylpropyl(meth) acrylate, the hydroxy-functional mono-, di- or tetra(meth) acrylates of polyhydric alcohols, such as trimethylolpropane, glycerol, pentaerythritol, dipentaerythritol, ethoxylated, propoxylated or alkoxylated trimethylolpropane, glycerol, pentaerythritol, dipentaerythritol and industrial mixtures thereof. In addition, isocyanate-reactive oligomeric or polymeric unsaturated compounds containing acrylate and/or methacrylate groups, alone or in combination with the abovementioned monomeric compounds, are suitable. The proportion of isocyanates which are partly reacted with isocyanate-reactive ethylenically unsaturated compounds, based on the isocyanate component a), is 0 to 99%, preferably 0 to 50%, particularly preferably 0 to 25% and very particularly preferably 0 to 15%, by weight.

It is also possible for the abovementioned isocyanate component a) to contain, completely or proportionately, isocyanates which are reacted completely or partially with blocking agents known to the person skilled in the art from coating technology. The following may be mentioned as an example of blocking agents: alcohols, lactams, oximes, malonic esters, alkyl acetoacetates, triazoles, phenols, imidazoles, pyrazoles and amines, such as, for example, butanone oxime, diisopropylamine, 1,2,4-triazole, dimethyl-1,2,4-triazole, imidazole, diethyl malonate, ethyl acetoacetate, acetone oxime, 3,5-dimethylpyrazole, ε-caprolactam, N-tert-butylbenzylamine, cyclopentanone carboxyethyl ester or any desired mixtures of these blocking agents.

It is very particularly preferable for the polyisocyanate component of the photopolymer formulation according to the invention to be an aliphatic polyisocyanate or a prepolymer with primary NCO groups.

All polyfunctional, isocyanate-reactive compounds which have on average at least 1.5 isocyanate-reactive groups per molecule can be used as polyol component b).

In the context of the present invention, isocyanate-reactive groups are preferably hydroxyl, amino or thio groups, and hydroxy compounds are particularly preferred.

Suitable polyfunctional, isocyanate-reactive compounds are, for example, polyester-, polyether-, polycarbonate-, poly(meth)acrylate- and/or polyurethanepolyols.

Suitable polyesterpolyols are, for example, linear polyesterdiols or branched polyesterpolyols, as are obtained in a known manner from aliphatic, cycloaliphatic or aromatic di- or polycarboxylic acids or their anhydrides with polyhydric alcohols having an OH-functionality of ≥2.

Examples of such di- or polycarboxylic acids or anhydrides are succinic, glutaric, adipic, pimelic, suberic, azelaic, sebacic, nonanedicarboxylic, decanedicarboxylic, terephthalic, isophthalic, o-phthalic, tetrahydrophthalic, hexahydrophthalic or trimellitic acid and acid anhydrides, such as o-phthalic, trimellitic or succinic anhydride or any desired mixtures thereof with one another.

Examples of such suitable alcohols are ethanediol, di-, tri- or tetraethylene glycol, 1,2-propanediol, di-, tri- or tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, 1,8-octanediol, 1,10-decanediol, 1,12-dodecanediol, trimethylolpropane, glycerol or any desired mixtures thereof with one another.

The polyesterpolyols may also be based on natural raw materials, such as castor oil. It is also possible for the polyesterpolyols to be based on homo- or copolymers of lactones, as can preferably be obtained by an addition reaction of lactones or lactone mixtures, such as butyrolactone, ε-caprolactone and/or methyl-ε-caprolactone, with hydroxy-functional compounds, such as polyhydric alcohols having an OH-functionality of ≥2 for example of the aforementioned type or of the polyetherpolyols described hereinbelow.

Such polyesterpolyols preferably have number average molar masses of 400 to 4000 g/mol, particularly preferably of 500 to 2000 g/mol. Their OH functionality is preferably 1.5 to 3.5, particularly preferably 1.8 to 3.0.

Suitable polycarbonatepolyols are obtainable in a manner known per se by reacting organic carbonates or phosgene with diols or diol mixtures.

Suitable organic carbonates are dimethyl, diethyl and diphenyl carbonate.

Suitable diols or mixtures comprise the polyhydric alcohols mentioned in connection with the polyester segments and having an OH functionality of ≥2, preferably 1,4-butanediol, 1,6-hexanediol and/or 3-methylpentanediol, or polyesterpolyols can be converted into polycarbonatepolyols.

Such polycarbonatepolyols preferably have number average molar masses of 400 to 4000 g/mol, particularly preferably of 500 to 2000 g/mol. The OH functionality of these polyols is preferably 1.8 to 3.2, particularly preferably 1.9 to 3.0.

Suitable polyetherpolyols are polyadducts of cyclic ethers with OH- or NH-functional starter molecules, said polyadducts optionally having a block structure.

Suitable cyclic ethers are, for example, styrene oxides, ethylene oxide, propylene oxide, tetrahydrofuran, butylene oxide, epichlorohydrin and any desired mixtures thereof.

Starters which may be used are the polyhydric alcohols mentioned in connection with the polyesterpolyols and having an OH functionality of ≥2 and primary or secondary amines and amino alcohols.

Preferred polyetherpolyols are those of the abovementioned type, exclusively based on propylene oxide or random or block copolymers based on propylene oxide with further 1-alkylene oxides, the proportion of 1-alkylene oxides being not higher than 80% by weight. In addition, poly(tetramethylene oxide)s which can be obtained, for example, from the ring-opening polymerization of tetrahydrofuran are suitable and mixtures of the polyols mentioned as being preferred are preferred. Propylene oxide homopolymers and random or block copolymers which have oxyethylene, oxypropylene and/or oxybutylene units are particularly preferred, the proportion of the oxypropylene units, based on the total amount of all oxyethylene, oxypropylene and oxybutylene units, accounting for at least 20% by weight, preferably at least 45% by weight. Here, oxypropylene and oxybutylene comprise all respective linear and branched C3- and C4-isomers.

Such polyetherpolyols preferably have number average molar masses of 250 to 10 000 g/mol, particularly preferably of 500 to 8500 g/mol and very particularly preferably of 600 to 4500 g/mol. The OH functionality is preferably 1.5 to 4.0, particularly preferably 1.8 to 3.1

In addition, aliphatic, araliphatic or cycloaliphatic di-, tri- or polyfunctional alcohol having molecular weights below 500 g/mol and containing 2 to 20 carbon atoms are useful as polyfunctional, isocyanate-reactive compounds as constituents of component b).

These can be for example ethylene glycol, diethylene glycol, triethylene glycol, tetraethylene glycol, dipropylene glycol, tripropylene glycol, 1,2-propanediol, 1,3-propanediol, 1,4-butanediol, neopentylglycol, 2-ethyl-2-butylpropanediol, trimethylpentanediol, positionally isomeric diethyloctanediols, 1,3-butylene glycol, cyclohexanediol, 1,4-cyclohexanedimethanol, 1,6-hexanediol, 1,2-cyclohexanediol, 1,4-cyclohexanediol, hydrogenated bisphenol A (2,2-bis(4-hydroxycyclohexyl)propane), (2,2-dimethyl-3-hydroxypropyl) 2,2-dimethyl-3-hydroxypropionate. Examples of suitable triols are trimethylolethane, trimethylolpropane or glycerol. Suitable higher-functional alcohols are ditrimethylolpropane, pentaerythritol, dipentaerythritol or sorbitol.

It is particularly preferable for the polyol component in the photopolymer formulation of the invention to be a difunctional polyether-, polyester or polyether-polyester block copolyester with primary OH functions.

The employed photoinitiators c) are typically initiators which are activatable by actinic radiation and which trigger a polymerization of the corresponding polymerizable groups. Photoinitiators are commercially available compounds known per se, which are classed as unimolecular (type I) and bimolecular (type II). These initiators are further used according to their chemical type for free-radical polymerization, anionic (or) cationic (or mixed) forms of the aforementioned polymerizations.

The photoinitiators c) may more particularly comprise an anionic, cationic or neutral dye and a co-initiator.

(Type I) systems for free-radical photopolymerization are for example aromatic ketone compounds, for example benzophenones combined with tertiary amines, alkylbenzophenones 4,4'-bis(dimethylamino)benzophenones (Michler's ketone), anthrone and halogenated benzophenones or mixtures thereof. Also suitable are (type II) initiators such as benzoin and its derivatives, benzil ketals, acylphosphine oxides, e.g. 2,4,6-trimethylbenzoyldiphenylphosphine oxide, bisacylophosphine oxides, phenylglyoxylic esters, camphorquinone, alpha-aminoalkylphenone, alpha,alpha-dialkoxyacetophenone, 1-[4-(phenylthio)phenyl]octane-1,2-dione-2-(O-benzoyl oxime) and alpha-hydroxyalkylphenone.

Similarly, the photoinitiator systems described in EP-A 0 223 587, consisting of a mixture of an ammonium arylborate and one or more dyes, can be used as photoinitiator. Examples of suitable ammonium arylborates are tetrabutylammonium tetrahexylborate, tetrabutylammonium triphenylhexylborate, tetrabutylammonium triphenylbutylborate, tetrabutylammonium trinapthylhexylborate, tetrabutylammonium tris(4-tert-butyl)phenylbutylborate, tetrabutylammonium tris(3-fluorophenyl)hexylborate, tetramethylammonium triphenylbenzylborate, tetra(n-hexyl)ammonium (sec-butyl) triphenylborate, 1-methyl-3-octylimidazolium dipentyldiphenylborate and tetrabutylammonium tris-(3-chloro-4-methylphenyl)hexylborate. Suitable dyes include for example new methylene blue, thionine, basic yellow, pinacynol chloride, rhodamine 6G, gallocyanine, ethyl violet, Victoria Blue R, Celestine Blue, quinaldine red, crystal violet, brilliant green, Astrazone Orange G, Darrow Red, pyronine Y, Basic Red 29, Pyrillium I, cyanine and methylene blue, azure A (Cunningham et al., RadTech'98 North America UV/EB Conference Proceedings, Chicago, Apr. 19-22, 1998).

The photoinitiators used for the anionic polymerization are generally (type I) systems and are derived from transition metal complexes of the first series. Chromium salts, for example trans-$Cr(NH_3)_2(NCS)_4^-$ (Kutal et al, Macromolecules 1991, 24, 6872) or ferrocenyl compounds (Yamaguchi et al. Macromolecules 2000, 33, 1152) must be mentioned here. A further possibility of anionc polymerization consists in the use of dyes, such as crystal violet leuconitrile or malchite green leuconitrile, which are capable of polymerizing cyanoacrylates by photolytic decomposition (Neckers et al. Macromolecules 2000, 33, 7761).

The photoinitiators used for cationic polymerization consist essentially of three classes: aryldiazonium salts, onium salts (here specifically: iodonium, sulphonium and selenonium salts) and organometallic compounds. Phenyldiazonium salts are able to produce a cation that initiates the polymerization when they are irradiated in the presence or in the absence of a hydrogen donor. The efficiency of the overall system is determined by the nature of the ion used as counter-ion to the diazonium compound. Preference is given here to $SbF_6^-$, $AsF_6^-$ or $PF_6^-$, which are not very reactive but may be expensive. These compounds are generally not very suitable for use in coating thin films, since the nitrogen released on exposure reduces the surface quality (pinholes) (Li et al., Polymeric Materials Science and Engineering, 2001, 84, 139).

Onium salts, specifically sulphonium salts and iodonium salts, are very widely used and also commercially available in many forms. The photochemistry of these compounds has been the subject of sustained interest. Iodonium salts when excited initially decompose homolytically and thus product a free radical and a free radical anion which stabilizes by hydrogen abstraction and releases a proton and then initiates the cationic polymerization (Dektar et al. J. Org. Chem. 1990, 55, 639; J. Org. Chem., 1991, 56. 1838). This mechanism makes it possible to use iodonium salts for free-radical photopolymerization also. Again, the choice of counter-ion is very important here and preference is likewise given to $SbF_6^-$, $AsF_6^-$ or $PF_6^-$. Otherwise, the choice of substitution for the aromatic moiety is fairly free with this structural class, being essentially determined by the availability of suitable starting synthons for the synthesis.

The sulphonium salts are compounds which decompose by Norrish (II) (Crivello et al., Macromolecules, 2000, 33, 825). The choice of counter-ion in the sulphonium salts again has a critical importance which is essentially reflected in the curing rate of the polymers. The best results are generally achieved with $SbF_6^-$ salts.

Since the self-absorption of iodonium and sulphonium salts is at <300 nm, these compounds have to be appropriately sensitized for the photopolymerization with near UV or short-wave visible light. This is accomplished by the use of more highly absorbing aromatics such as, for example, anthracene and derivatives (Gu et al., Am. Chem. Soc. Polymer Preprints, 2000, 41 (2), 1266) or phenothiazine and/or its derivatives (Hua et al, Macromolecules 2001, 34, 2488-2494).

It can be advantageous to use mixtures of these compounds. Depending on the radiation source used for curing, type and concentration has to be adapted to photoinitiator in a manner known to a person skilled in the art. Further particulars are available for example from P. K. T. Oldring (Ed.), Chemistry & Technology of UV & EB Formulations For Coatings, Inks & Paints, Vol. 3, 1991, SITA Technology, London, pp. 61-328.

Preferred photoinitiators c) are mixtures of tetrabutylammonium tetrahexylborate, tetrabutylammonium triphenylhexylborate, tetrabutylammonium triphenylbutylborate, tetrabutylammonium trinapthylbutylborate, tetrabutylammonium tris(4-tertbutyl)phenylbutylborate, tetrabutylammonium tris(3-fluorophenyl)hexylborate ([191726-69-9], CGI 7460, product from Ciba Inc, Basle) and tetrabutylammonium tris(3-chloro-4-methylphenyl)hexylborate ([1147315-11-4], CGI 909, product from Ciba Inc, Basle) with dyes such as, for example, Astrazone Orange G, methylene blue, new methylene blue, azure A, pyrillium I, safranine O, cyanine, gallocyanine, brilliant green, crystal violet, ethyl violet and thionine.

In a particularly preferred embodiment of the photopolymer formulation according to the invention, the photoinitiator consists of a combination of dyes having absorption spectra covering at least partly the spectral region from 400 to 800 nm, with at least one suitable coinitiator.

Particularly high refractive index contrasts are obtainable when the photopolymer formulation, in addition to the writing monomers of formula (I) according to the invention, preferably contains an acrylate- or methacrylate-functional writing monomer as further writing monomer d). Particular preference here is given to monofunctional writing monomers, more particularly monofunctional urethane(meth)acrylates as described in US 2010/0036013 A1.

An increase in the maximum refractive index contrast is also obtainable with a photopolymer formulation which additionally comprises plasticizers e), preferably plasticizers according to the general formula (II)

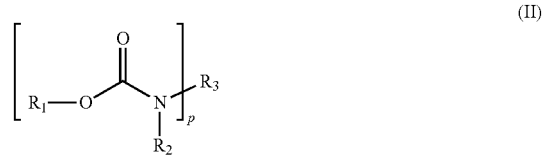

(II)

where p is ≥1 and ≤8 and $R^1$, $R^2$, $R^3$ are hydrogen and/or independently linear, branched, cyclic or heterocyclic unsubstituted or else optionally heteroatom-substituted organic radicals, wherein preferably at least one of the radicals $R^1$, $R^2$, $R^3$ is substituted with at least a fluorine atom and more preferably $R^1$ is an organic radical having at least one fluorine atom.

The plasticizers of formula II are fluorourethanes obtainable by the reaction of a polyisocyanate comprising biuret, isocyanurate, uretdione, polyurea, iminooxadiazinediones or oxadiazadione and having at least one free isocyanate group with an alcohol, wherein the polyisocyanate and/or the alcohol is substituted with at least one fluorine atom.

The fluorourethanes of formula (II) are further obtainable by reaction of isocyanates of formula $R[NCO]_n$ with fluorinated alcohols in a relative stoichiometric ratio with urethane formation.

Preferred isocyanates of formula $R[NCO]_n$ are methyl isocyanate, ethyl isocyanate, the isomeric propyl isocyanates, the isomeric butyl isocyanates, the isomeric pentyl isocyanates, the isomeric hexyl isocyanates, the isomeric heptyl isocyanates, the isomeric octyl isocyanates, the isomeric nonyl isocyanates, the isomeric decyl isocyanates, stearyl isocyanate, cyclopropyl isocyanate, cyclobutyl isocyanate, cyclopentyl isocyanate, cyclohexyl isocyanate, cycloheptyl isocyanate, 2-methylpentane 1,5-diisocyanate (MPDI), dodecamethylene diisocyanate, 1,8-diisocyanato-4-(isocyanatomethyl)octane (TIN), 6-diisocyanatohexane (HDI, Desmodur H), 1-isocyanato-3,3,5-trimethyl-5-isocyanatomethylcyclohexane (IPDI, Desmodur I), 2,4,4-trimethylhexane 1,6-diisocyanate (TMDI), dicyclohexylmethane diisocyanate (Desmodur W), hexahydrotolylene diisocyanate (H6TDI), 1,3-bis(isocyanatomethyl)cyclohexane, Desmodur LD, Desmodur N 100, Desmodur N3200, Desmodur N3300, Desmodur N3350, Desmodur N3368, Desmodur N3375, Desmodur N3390, Desmodur N3400, Desmodur N3600, Desmodur N3600, Desmodur N3790, Desmodur N3800, Desmodur N3900, Desmodur N50, Desmodur N75, Desmodur NZ1, Desmodur PL340, Desmodur PL350, Desmodur PM76, Desmodur BL3175, Desmodur BL3272, Desmodur BL3370, Desmodur BL3475, Desmodur BL4265, Desmodur BL5375, Desmodur BLXP2677, Desmodur DA-L, Desmodur DN, Desmodur E 305, Desmodur E3265, Desmodur E3370, Baymicron OXA, Desmodur VP LS 2078/2, Desmodur VP LS 2114/1, Desmodur VP LS 2257, Desmodur VP LS 2352/1, Desmodur VP LS 2371, Desmodur VP LS 2376/1, Desmodur XP 2406, Desmodur XP 2489, Desmodur XP 2565, Desmodur XP 2580, Desmodur XP 2599, Desmodur XP 2617, Desmodur XP 2626, Desmodur XP 2675, Desmodur XP 2679, Desmodur XP 2714, Desmodur XP 2730, Desmodur XP 2731, Desmodur XP 2742, Desmodur XP 2748, Desmodur Z 4470 or mixtures thereof.

Particularly preferred isocyanates of the formula R[NCO]$_n$ are isomeric propyl isocyanates, the isomeric butyl isocyanates, the isomeric pentyl isocyanates, the isomeric hexyl isocyanates, the isomeric heptyl isocyanates, the isomeric octyl isocyanates, the isomeric nonyl isocyanates, the isomeric decyl isocyanates, stearyl isocyanate, 1,8-diisocyanato-4-(isocyanatomethyl)octane (TIN), 6-diisocyanatohexane (HDI, Desmodur H), 1-isocyanato-3,3,5-trimethyl-5-isocyanatomethylcyclohexane (IPDI, Desmodur I), 2,4,4-trimethylhexane 1,6-diisocyanate (TMDI), dicyclohexylmethane diisocyanate (Desmodur W), hexahydrotolylene diisocyanate (H6TDI), 1,3-bis(isocyanatomethyl)cyclohexane, Desmodur LD, Desmodur N3400, Desmodur N3600, Desmodur N3600, Baymicron OXA or mixtures thereof.

Very particularly preferred isocyanates of the formula R[NCO]$_n$ are isopropyl isocyanate, n-butyl isocyanate, n-hexyl isocyanate, n-octyl isocyanate, n-decyl isocyanate, cyclohexyl isocyanate, stearyl isocyanate, 1,8-diisocyanato-4-(isocyanatomethyl)octane (TIN), 6-diisocyanatohexane (HDI, Desmodur H), 1-isocyanato-3,3,5-trimethyl-5-isocyanatomethylcyclohexane (IPDI, Desmodur I), 2,4,4-trimethylhexane 1,6-diisocyanates (TMDI), dicyclohexylmethane diisocyanate (Desmodur W), hexahydrotolylene diisocyanate (H6TDI), 1,3-bis(isocyanatomethyl)cyclohexane, Desmodur LD, Desmodur N3400, Desmodur N3600, Desmodur N3900, Baymicron OXA or mixtures thereof.

The possible choice of the fluorinated alcohols is broad, and it is preferable to use primary or secondary, mono-, di- or trifunctional alcohols having a fluorine content of 30% to 82% of fluorine, particularly preferably having a fluorine content of 40% to 80% of fluorine and especially preferably having a fluorine content of 49% to 75% of fluorine.

The reaction of isocyanates with alcohols of the type mentioned in each case above for the preparation of the fluorourethanes (II) is a urethanization. The reaction can be effected with the aid of the catalysts known for accelerating isocyanate addition reactions, such as, for example, tertiary amines, tin, zinc, iron or bismuth compounds, in particular triethylamine, 1,4-diazabicyclo[2.2.2]octane, bismuth octoate, zinc octoate or dibutyltin dilaurate, which can be initially introduced or metered in later.

The fluorourethanes of formula (II) may have a content of isocyanate groups (M=42 g/mol) or free isocyanate radical monomers of less than 0.5% by weight, preferably of less than 0.2% by weight, particularly preferably of less than 0.1% by weight.

The fluorourethanes of formula (II) further contain below 1% by weight, preferably below 0.5% by weight and more preferably below 0.2% by weight of unconverted hydroxy-functional compounds and have a fluorine content of 10-80% by weight of fluorine, preferably 12.5-75% by weight of fluorine, more preferably 15-70% by weight of fluorine and more particularly preferably 17.5-65% by weight of fluorine. The fluorourethanes of formula II have a refractive index $n^{20}{:}_D$ of $\leq 1.4600$, preferably of $\leq 1.4500$, more preferably of $\leq 1.4400$ and more particularly preferably of $\leq 1.4300$.

In a further preferred embodiment of the invention, the photopolymer formulation contains 10% to 89.999% by weight and preferably 20% to 70% by weight of matrix polymers consisting of compounds of component a) and of component b), 10% to 60% by weight and preferably 25% to 50% by weight of writing monomers, 0.001% to 5% by weight of photoinitiators and optionally 0% to 4% by weight and preferably 0% to 2% by weight of catalysts, 0% to 5% by weight and preferably 0.001% to 1% by weight of free-radical stabilizers, 0% to 40% by weight and preferably 10% to 30% by weight of plasticizers and 0% to 5% by weight and preferably 0.1% to 5% by weight of further additives, the sum total of all the constituents being 100% by weight.

Particular preference is given to using photopolymer formulations including 20% to 70% by weight of matrix polymers consisting of compounds of component a) and component b), 25% to 50% by weight of writing monomers, 0.001% to 5% by weight of photoinitiators, 0% to 2% by weight of catalysts, 0.001% to 1% by weight of free-radical stabilizers, optionally 10% to 30% by weight of the above-described fluorourethanes of formula II and optionally 0.1 to 5% by weight of further additives.

The invention further provides for the use of a photopolymer formulation according to the invention for producing holographic media especially for recording in-line, off-axis, full-aperture, transfer, white light, transmission, Denisyuk, off-axis reflection or edge-lit holograms and also holographic stereograms.

The invention still further provides for the use of a photopolymer formulation according to the invention for producing holographic media which are processable to holograms in the entire visible and near UV region (300-800 nm) by appropriate exposure processes for optical applications. Visual holograms comprise any hologram which is recordable by processes known to a person skilled in the art. This definition includes inter alia in-line (Gabor) holograms, off-axis holograms, full-aperture transfer holograms, white light transmission holograms ("rainbow holograms), Denisyuk holograms, off-axis reflection holograms, edge-lit holograms and also holographic stereograms. Preference is given to reflection holograms, edge-lit holograms, transmission holograms.

Possible optical functions of the holograms obtainable using the photopolymer formulations of the present invention correspond to the optical functions of light elements such as lenses, mirrors, deflectors, filters, diffuser screens, diffraction elements, light conductors, waveguides, projection screens and/or masks. In addition, several such optical functions can be combined in any one such hologram, for example such that light is diffracted in a different direction depending on its angle of incidence. Such subassemblies can be used to construct autostereoscopic electronic displays whereby a stereoscopic visual impression can be experienced without further aids such as polarizing or shutter glasses for example.

Frequently, these optical elements show a specific frequency selectivity, depending on how the holograms were exposed and on the dimensions of the hologram. This is particularly important when using monochromatic sources of light such as LED or laser light. One hologram per complementary colour (RGB) is needed to guide light frequency-selectively and at the same time provide full-colour displays. Therefore, in certain display subassemblies, multiple holograms must be exposed inside each other in one photopolymer film.

In addition, the photopolymer formulations of the invention can also be used to produce holographic pictures or images, for example for personal portraits, biometric representations in security documents or generally of images or image structures for advertising, security labels, brand protection, branding, labels, design elements, decorations, illustrations, multi-journey tickets, images and the like, and also images which can represent digital data, inter alia also in combination with the products described above. Holographic images can give the impression of a three-dimensional image, but they may also represent image sequences, short films or a number of different objects, depending on the angle from which they are illuminated, the light source (including moving light source) with which they are illuminated, etc. It is because of these diverse design possibilities that holograms, more particularly volume holograms, constitute an attractive technical solution for the abovementioned use.

The photopolymer formulations can be used more particularly as a holographic medium in the form of a film. A layer of a material or assembly of materials which is transparent to light in the visible spectrum (transmission greater than 85% in the wavelength range from 400 to 780 nm), as a support, is coated one- or both-sidedly with a layer of the photopolymer formulation and, optionally, a covering layer is applied on top of the photopolymer layer or layers.

Preferred materials or assemblies of materials for the support are based on polycarbonate (PC), polyethylene terephthalate (PET), polybutylene terephthalate, polyethylene, polypropylene, cellulose acetate, cellulose hydrate, cellulose nitrate, cycloolefin polymers, polystyrene, polyepoxides, polysulphone, cellulose triacetate (CTA), polyamide, polymethyl methacrylate, polyvinyl chloride, polyvinyl butyral or polydicyclopentadiene or mixtures thereof. They are more preferably based on PC, PET and CTA. Assemblies of materials can be laminates of self-supporting polymeric sheets, or coextrudates. Preferred assemblies of materials are duplex and triplex films constructed according to one of the schemes A/B, A/B/A or A/B/C. Particular preference is given to PC/PET, PET/PC/PET and PC/TPU (TPU=thermoplastic polyurethane).

As an alternative to the abovementioned plastics support, it is also possible to use planar glass plates, which are used particularly for large-area accurately imaging exposures, for example for holographic lithography (Ng, Willie W.; Hong, Chi-Shain; Yariv, Amnon Holographic interference lithography for integrated optics. IEEE Transactions on Electron Devices (1978), ED-25(10), 1193-1200, ISSN:0018-9383).

The materials or assemblies of materials of the support may have an anti-stick, antistatic, hydrophobic or hydrophilic finish on one or both sides. On the side facing the photopolymer layer, the modifications mentioned serve the purpose of making it possible to remove the photopolymer layer from the support non-destructively. A modification of that side of the support which faces away from the photopolymer layer serves to ensure that the media of the present invention meet specific mechanical requirements, for example in relation to processing in roll laminators, more particularly in roll-to-roll processes.

Figure 2:
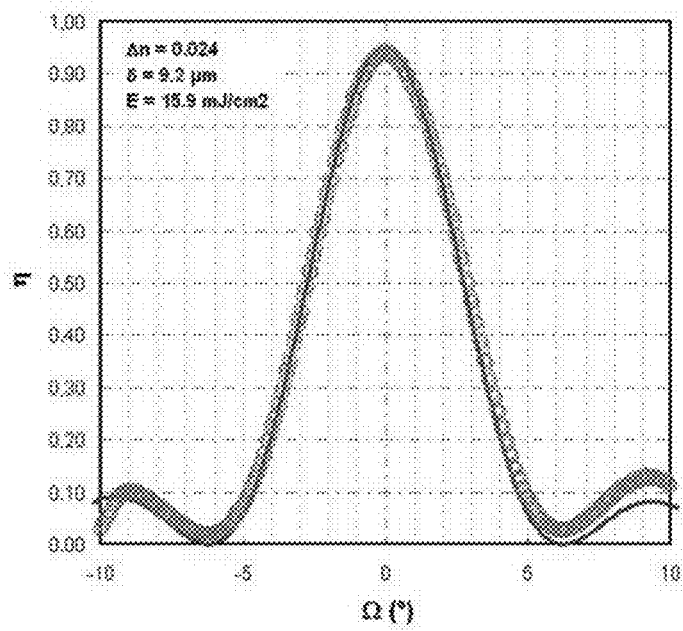

The examples which follow illustrate the invention.
In the drawing,
FIG. 1 shows the geometry of a holographic media tester (HMT) at $\lambda$=532 nm (DPSS Laser=Diode Pumped Solid State Laser) and FIG. 2 shows the measured diffraction efficiency $\eta$ as circles versus the angle detuning $\Delta\Omega$ and the fitting of the Kogelnik theory as a continuous line. What is shown is Comparative Example 2

Methods of Measurement:
Refractive Index Determination:

The refractive index of high-viscosity and solid products was measured at a wavelength of 589 nm by obtaining the refractive index n from the transmission and reflection spectra as a function of the wavelength of the sample. To this end, about 100-300 nm thick films of the samples were applied to quartz glass supports from a five weight percent solution in ethyl acetate by spin coating. The transmission and reflection spectrum of this layer packet was measured with a spectrometer from STEAG ETA-Optik, CD-Measurement System ETA-RT, and the layer thickness and the spectrial course of n were then fitted to the measured transmission and reflection spectra. This is accomplished by the internal software of the spectrometer and additionally requires the n data of the quartz glass substrate, which were determined beforehand in a blank measurement.

For liquid products, an Abbe refractrometer is used for refractive index determination at 589 nm. In detail, 3 drops of the product were applied to the cleaned measuring prism of the instrument, the illumination prism was closed and conditioned to 20° C. within 2 minutes.

Thereafter, the light-dark boundary is sharply adjusted onto the cross-hairs of the refractometer in the observation field. Once the value set remained constant, the refractive index was read off to four places after the decimal. A duplicate determination was carried out. Deviations up to 0.0002 scale divisions were admissible.

Haze Measurement

Haze was measured in accordance with ASTM D 1003. Haze is the percentage fraction of transmitted light that differs from the incident bundle of light by more than 2.5° on average.

To measure haze, the holographic coupons were cleaned from the outside before the measurement to avoid any distortion of the result by fingerprints and dirt on the glasses. Then, the coupons were placed in a Haze-Gard-Plus instrument from Byk-Gardner for measurement.

Isocyanate Content

The reported NCO values (isocyanate contents) were determined in accordance with DIN EN ISO 11909.

The complete conversion of NCO groups, or their absence in a reaction mixture, was detected by IR spectroscopy. Complete conversion was accordingly assumed when there was no NCO band (2261 cm$^{-1}$) in the IR spectrum of the reaction mixture.

Solids Content

The tare weight of an uncoated can lid and of a paperclip were determined. Then, about 1 g of the sample to be investigated was uniformly distributed with the suitably bent paperclip after weighing into the can lid. The paperclip remained in the sample for the measurement. The original weight was determined, then the sample was heated in a laboratory oven at 125° C. for 1 hour and finally the final weight was determined. The solids content was determined using the following equation: final weight [g]*100/original weight [g]=% by weight of solids.

Measurement of the Holographic Properties DE and Δn of the Holographic Media by Means of Two-Beam Interference in Transmission Arrangement The media produced were tested with regard to their holographic properties by means of a measuring arrangement according to FIG. 1, as follows:

FIG. 1 shows the holographic experimental set-up used for measuring the diffraction efficiency (DE) of the media, where M=mirror, S=shutter, SF=spatial filter, CL=collimator lens, λ/2=λ/2 plate, PBS=polarization-sensitive beam splitter, D=detector, I=iris diaphragm, $\alpha_0$=−22.3°, $\beta_0$=22.3° are the angles of incidence of the coherent beams, measured outside the sample (outside the medium). RD=reference direction of turntable.

The beam of a DPSS laser (emission wavelength 532 nm) was converted with the aid of the spatial filter (SF) and together with the collimation lens (CL) into a parallel homogeneous beam. The final cross sections of the signal and reference beam are established by the iris diaphragms (I). The diameter of the iris diaphragm opening is 0.4 cm. The polarization-dependent beam splitters (PBS) split the laser beam into two coherent equally polarized beams. Via the λ/2 plates, the power of the reference beam was adjusted to 2.0 mW and the power of the signal beam to 2.0 mW. The powers were determined using the semiconductor detectors (D) with sample removed. The angle of incidence ($\alpha_0$) of the reference beam is −22.3° and the angle of incidence ($\beta_0$) of the signal beam is 22.3°. The angles are measured starting from the sample normal to the beam direction. According to FIG. 1, $\alpha_0$ therefore has a negative sign and $\beta_0$ a positive sign. At the location of the sample (medium), the interference field of the two overlapping beams produced a grating of light and dark strips which are parallel to the angle dissectors of the two beams incident on the sample (transmission hologram). The strip spacing Λ, also referred to as grating period, in the medium is ~700 nm (the refractive index of the medium assumed to be ~1.504).

Holograms were recorded in the medium in the following manner:
  both shutters (S) are opened for the exposure time t.
  Thereafter, with closed shutters (S), the medium was allowed a time of 5 minutes for diffusion of the as yet unpolymerized writing monomers.

The holograms recorded were now read in the following manner. The shutter of the signal beam remained closed. The shutter of the reference beam was open. The iris diaphragm of the reference beam was closed to a diameter of <1 mm. This ensured that the beam was always completely in the previously recorded hologram for all angles of rotation (Ω) of the medium. The turntable, under computer control, now covered the angle range from $\Omega_{min}$ to $\Omega_{max}$ with an angle step width of 0.05°. Ω is measured from the sample normal to the reference direction of the turntable. The reference direction (Ω=0) of the turntable is obtained when the angle of incidence of the reference beam and that of the signal beam have the same magnitude, i.e. $\alpha_0$=−22.3° and $\beta_0$=22.3°, on recording of the hologram. In general, the following is true for the interference field during recording of a symmetrical transmission hologram ($\alpha_0$=−$\beta_0$):

$$\alpha_0 = \theta_0$$

$\theta_0$ is the semiangle in the laboratory system outside the medium. In this case, $\theta_0$=−22.3°. At each angle of rotation Ω approached, the powers of the beam transmitted in the zero order were measured by means of the corresponding detector D and the powers of the beam diffracted in the first order were measured by means of the detector D. The diffraction efficiency was obtained at each angle Ω approached as the quotient of:

$$\eta = \frac{P_D}{P_D + P_T}$$

$P_D$ is the power in the detector of the diffracted beam and $P_T$ is the power in the detector of the transmitted beam.

By means of the method described above, the Bragg curve (it describes the diffraction efficiency η as a function of the angle of rotation Ω of the recorded hologram) was measured and was stored in a computer. In addition, the intensity transmitted in the zero order was also plotted against the angle of rotation Ω and stored in a computer.

The central diffraction efficiency (DE=η0) of the hologram was determined at Ω=0.

The refractive index contrast Δn and the thickness d of the photopolymer layer was then fitted to the measured Bragg curve using Coupled Wave Theory (see; H. Kogelnik, The Bell System Technical Journal, Volume 48, November 1969, Number 9 page 2909-page 2947). The method of evaluation will now be described:

According to Kogelnik, the following is true for the Bragg curve η(Ω) of a transmission hologram:

$$\eta = \frac{\sin^2\left(\sqrt{\nu^2 + \xi^2}\right)}{1 + \frac{\xi^2}{\nu^2}}$$

where:

$$\nu = \frac{\pi \cdot \Delta n \cdot d}{\lambda \cdot \sqrt{|c_s \cdot c_r|}}$$

$$\xi = -\frac{d}{2 \cdot c_s} \cdot DP$$

$$c_s = \cos(\vartheta)$$

$$c_r = \cos(\vartheta)$$

$$DP = \frac{\pi}{\Lambda} \cdot \left(-2 \cdot \sin(\vartheta) - \frac{\lambda}{n \cdot \Lambda}\right)$$

$$\Lambda = -\frac{\lambda}{2 \cdot n \cdot \sin(\alpha)}$$

On reading the hologram ("reconstruction"), the following is true as described analogously above:

$$\partial_0 = \theta_0 + \Omega$$

$$\sin(\partial_0) = n \cdot \sin(\partial)$$

Under the Bragg condition, the "dephasing" DP=0. Accordingly:

$$\alpha_0 = \theta_0$$

$$\sin(\alpha_0) = n \cdot \sin(\alpha)$$

ν is the grating thickness and ζ is the detuning parameter of the refractive index grating which was recorded. n is the average refractive index of the photopolymer and was set at 1.504. λ is the wavelength of the laser light in vacuo.

The central diffraction efficiency (DE=η0) is then obtained for ζ=0 as:

$$DE = \sin^2(c) = \sin^2\left(\frac{\pi \cdot \Delta n \cdot d}{\lambda \cdot \cos(\alpha)}\right)$$

The measured data of the diffraction efficiency and the theoretical Bragg curve are plotted against the angle of rotation Ω as shown in FIG. 2.

Since DE is known, the shape of the theoretical Bragg curve according to Kogelnik is determined only by the thickness d of the photopolymer layer. Δn is subsequently corrected for a given thickness d via DE such that measurement and theory of DE always agree. d is then adjusted until the angle positions of the first secondary minima and the heights of the first secondary maxima of the theoretical Bragg curve agree with the angle positions of the first secondary minima and the heights of the first secondary maxima of the measured Bragg curve.

FIG. 2 shows the theoretically calculated and experimentally fitted Bragg curve η according to Coupled Wave Theory (also known as Kogelnik theory) as continuous line and for comparison the experimentally determined diffraction efficiency (in circular symbols) plotted against the angle of rotation Ω.

For any one formulation, this procedure was possibly repeated several times for different exposure times t on different media in order to determine the average energy dose of the incident laser beam at which Δn reaches the saturation value during recording of the hologram. The average energy dose E is obtained from the powers of the two part-beams coordinated with the angles $\alpha_0$ and $\beta_0$ (reference beam with $P_r$=2.00 mW and signal beam with $P_s$=2.00 mW), the exposure time t and the diameter of the iris diaphragm (0.4 cm), as follows:

$$E(\text{mJ}/\text{cm}^2) = \frac{2 \cdot [P_r + P_s] \cdot t(s)}{\pi \cdot 0.4^2 \text{ cm}^2}$$

Chemicals:

Where known, the CAS number is in each case reported between angular parentheses.

| | |
|---|---|
| 2-[(Biphenyl-2-yloxy)methyl]oxirane | [7144-65-2] - American Custom Chemicals Corporation, San Diego Ca, USA |
| 2-Isocyanatoethyl acrylate | [13641-96-8] - Karenz ® AOI, SHOWA DENKO K.K., Fine Chemicals Group, Specialty Chemicals Department, Chemicals Division, Japan |
| 1,2-Ethanedithiol | [540-63-6] - Merck Schuchardt OHG, Hohenbrunn, Germany |
| 1,3-Propanedithiol | [109-80-8] - Merck Schuchardt OHG, Hohenbrunn, Germany |
| 1,4-Butanedithiol | [1191-08-8] - SAFC, St. Louis, USA |
| 2,3-Butanedithiol | [4532-64-3] - Sigma-Aldrich Chemie GmbH, Steinheim, Germany |
| 1,6-Hexanedithiol | [1191-43-1] - SAFC, St. Louis, USA |
| 2,2'-Oxydiethanethiol | [2150-02-9] - ABCR GmbH & Co KG, Karlsruhe, Germany |
| 2,2'- Sulphanediyldiethanethiol | DMDES - Toyo Kasei Kogyo Co. Ltd, Takasago-City, Hyogo, Japan |
| 1,2-bis(2-Mercaptoethoxy)ethane | [14970-87-7] - Sigma-Aldrich Chemie GmbH, Steinheim, Germany |
| 1,10-Decanedithiol | [1191-67-9] - ABCR GmbH & Co KG, Karlsruhe, Germany |
| Ethylene glycol dimercaptoacetate | [123-81-9] - Merck Schuchardt OHG, Hohenbrunn, Germany |
| 4,4'-Sulphanediyldibenzenethiol | [19362-77-7] - Sigma-Aldrich Chemie GmbH, Steinheim, Germany |
| 2,3-Disulphanylpropan-1-ol | [59-52-9] - Acros Organics, New Jersey, USA |
| 1-Isocyanato-2-(phenylsulphanyl)benzene | [13739-55-4] - APAC Pharmceuticals, Columbia MD, USA |
| 1-Isocyanato-3-(methylsulphanyl)benzene | [28479-19-8]- Sigma-Aldrich Chemie GmbH, Steinheim, Germany |
| Tris(p-isocyanatophenyl) thiophosphate | Desmodur ® RFE, product from Bayer MaterialScience AG, Leverkusen, Germany |
| 3-Phenylphenol | [580-51-8] - Acros Organics, New Jersey, USA |
| Potassium carbonate | Sigma-Aldrich Chemie GmbH, Steinheim, Germany |
| Epibromohydrin | [3132-64-7]- Sigma-Aldrich Chemie GmbH, Steinheim, Germany |
| Triphenylphosphine | [603-35-0] ABCR GmbH & Co KG, Karlsruhe, Germany |
| 1-Butyl-3-Methylimidazolium bromide | [85100-77-2] - ABCR GmbH & Co KG, Karlsruhe, Germany |
| Dibutyltin dilaurate | [77-58-7] - Desmorapid Z urethanization catalyst, Bayer MaterialScience AG, Leverkusen, Germany |
| Fomrez ® UL 28 | Urethanization catalyst, commercial product from Momentive Performance Chemicals, Wilton, CT, USA. |
| Addocat ® SO | A tin-based catalyst from RheinChemie, Mannheim, Germany |

| | |
|---|---|
| Desmodur ® N 3900 | Product from Bayer MaterialScience AG, Leverkusen, Germany, hexane diisocyanate-based polyisocyanate, fraction of imino-oxadiazinedione at least 30%, NCO content: 23.5%. |
| CGI-909 | Tetrabutylammonium tris(3-chloro-4-methylphenyl) (hexyl)borate, [1147315-11-4] is a product from BASF SE (formerly Ciba Inc.). |
| Trimethylhexamethylene diisocyanate | [28679-16-5] - ABCR GmbH & Co KG, Karlsruhe, Germany |
| 1H,1H-7H-Perfluoroheptan-1-ol | [335-99-9] - ABCR GmbH & Co KG, Karlsruhe, Germany |
| Crystal violet | [548-62-9] Sigma-Aldrich Chemie GmbH, Steinheim, Germany |
| Irgacure ® 250 | [344562-80-7], Iodonium, (4-methylphenyl)[4-(2-methylpropyl) phenyl]-, hexafluorophosphate(1-) product from BASF SE (formerly Ciba Inc.). |

Inventive Writing Monomers:
General Method of Preparing the Dithiol-Oxirane Adducts (Example 1a-12a)

The oxirane and the catalyst were initially charged to a three-neck flask equipped with KPG stirrer and stirring motor and also drier tube. After heating to 60 to 80° C., the dithiol was added dropwise. Stirring was then continued at the stated temperature until a >95% conversion of the oxirane group was detectable in the $^1$H NMR spectrum, or until oxirane groups were no longer detectable in the $^1$H NMR spectrum.

Example 1a 3,3'-(Ethane-1,2-diyldisulphanediyl)bis[1-(biphenyl-2-yloxy)propan-2-ol]

Reactants: 14.3 g of 2-[(biphenyl-2-yloxy)methyl]oxirane
 34 mg of 1-butyl-3-methylimidazolium bromide
 2.8 g of 2-ethanedithiol
Conditions: Reaction temperature 70° C.; addition of dithiol within 1 hour, reaction time 19 hours
 A clear colourless viscous liquid was obtained.
 $^1$H NMR (CDCl$_3$, 400 MHz): δ (1H)=7.45 (d, 2H), 7.38 (t, 2H), 7.32 (m, 3H), 7.16 (t, 1H), 6.97 (d, 1H), 3.90-4.05 (m, 3H), 2.60-2.75 (m, 3H), 2.55 (dd, 1H), 2.45 (t, 1H, OH).

Example 2a 3,3'-(Propan-1,3-diyldisulphanediyl)bis[1-(biphenyl-2-yloxy)propan-2-ol]

Reactants: 14.3 g of 2-[(biphenyl-2-yloxy)methyl]oxirane
 33 mg of 1-butyl-3-methylimidazolium bromide
 3.2 g of 1,3-propanedithiol
Conditions: Addition within 30 minutes at 60° C. then 80° C., reaction time 20 h
 A clear colourless viscous liquid was obtained.
 $^1$H NMR (CDCl$_3$, 400 MHz): δ (1H)=7.45 (d, 4H), 7.38 (t, 6H), 7.32 (m, 6H), 7.16 (t, 2H), 6.97 (d, 2H), 3.98 (d, 4H), 3.92 (m, 2H), 2.64 (dd, 2H), 2.48-2.59 (m, 8H), 1.57 (p, 2H)

Example 3a 3,3'-(Butane-1,4-diyldisulphanediyl)bis[1-(biphenyl-2-yloxy)propan-2-ol]

Reactants: 16.7 g of 2-[(biphenyl-2-yloxy)methyl]oxirane
 42 mg of 1-butyl-3-methylimidazolium bromide
 4.3 g 1,4-butanedithiol
Conditions: Reaction temperature 80° C., reaction time 48.5 h
 A clear colourless viscous liquid was obtained.
 $^1$H NMR (CDCl$_3$, 400 MHz): δ (1H)=7.45 (d, 2H), 7.38 (t, 2H), 7.32 (m, 3H), 7.16 (t, 1H), 6.97 (d, 1H), 4.05 (d, 2H), 3.95 (m, 1H), 2.65 (dd, 1H), 2.58 (dd, 1H), 2.4-2.55 (m, 2H), 1.5-1.65 (m, 2H)

Example 4a 3,3'-(Butane-2,3-diyldisulphanediyl)bis[1-(biphenyl-2-yloxy)propan-2-ol]

Reactants: 14.3 g of 2-[(biphenyl-2-yloxy)methyl]oxirane
 36 mg of 1-butyl-3-methylimidazolium bromide
 3.7 g of 2,3-butanedithiol
Conditions: Reaction temperature 60° C. during dropwise addition, 80° C., reaction time 48.5 h
 A clear colourless viscous liquid was obtained.
 $^1$H NMR (CDCl$_3$, 400 MHz): δ (1H)=7.45 (d, 2H), 7.38 (t, 2H), 7.32 (m, 3H), 7.16 (t, 1H), 6.97 (d, 1H), 4.05 (d, 2H), 3.95 (m, 1H), 2.65 (dd, 1H), 2.58 (dd, 1H), 2.4-2.55 (m, 2H), 1.5-1.65 (m, 2H)

Example 5a 3,3'-(Hexane-1,6-diyldisulphanediyl)bis[1-(biphenyl-2-yloxy)propan-2-ol]

Reactants: 14.3 g of 2-[(biphenyl-2-yloxy)methyl]oxirane
 38 mg of 1-butyl-3-methylimidazolium bromide
 4.5 g of 1,6-hexanedithiol
Conditions: Reaction temperature 60° C. during dropwise addition, 70° C., reaction time: 25 h
 A clear colourless viscous liquid was obtained.
 $^1$H NMR (CDCl$_3$, 400 MHz): δ (1H)=7.45 (d, 2H), 7.38 (t, 2H), 7.32 (m, 3H), 7.16 (t, 1H), 6.97 (d, 1H), 4.05 (d, 2H), 3.95 (m, 1H), 2.65 (dd, 1H), 2.58 (dd, 1H), 2.45-2.52 (m, 3H), 1.5 (m, 2H), 1.35 (m, 2H)

Example 6a 3,3'-[Oxybis(ethane-2,1-diylsulphanediyl)]bis[1-(biphenyl-2-yloxy)propan-2-ol]

Reactants: 14.3 g of 2-[(biphenyl-2-yloxy)methyl]oxirane
 37 mg of 1-butyl-3-methylimidazolium bromide
 3.9 g 2,2'-Oxydiethanethiol Conditions: Reaction temperature 60° C. during dropwise addition, then 25 h reaction time at 70° C. then 24 h at 80° C.

A clear colourless viscous liquid was obtained.

$^1$H NMR (CDCl$_3$, 400 MHz): δ (1H)=7.45 (d, 2H), 7.38 (t, 2H), 7.32 (m, 3H), 7.16 (t, 1H), 6.97 (d, 1H), 3.9-4.05 (m, 3H), 3.55 (t, 2H), 2.87 (t, 1H, OH), 2.55-2.85 (m, 4H).

Example 7a 1,16-Bis(biphenyl-2-yloxy)-7,10-dioxa-4,13-dithia-hexadecane-2,15-diol Reactants: 14.3 g of 2-[(biphenyl-2-yloxy)methyl]oxirane
39 mg of 1-butyl-3-methylimidazolium bromide
5.2 g of 1,2-bis(2-mercaptoethoxy)ethane
Conditions: Reaction temperature 60° C. during dropwise addition, then 25 h reaction time at 70° C. then 19.5 h at 80° C.

A clear pale yellow product was obtained.

$^1$H NMR (CDCl$_3$, 400 MHz): δ (1H)=7.45 (d, 2H), 7.38 (t, 2H), 7.32 (m, 3H), 7.16 (t, 1H), 6.97 (d, 1H), 3.9-4.0 (m, 3H), 3.55 (m, 4H), 2.88 (m, 1H, OH), 2.55-2.65 (m, 4H).

Example 8a 3,3'-(Decane-1,10-diyldisulphanediyl)bis[1-(biphenyl-2-yloxy)propan-2-ol]

Reactants: 14.3 g of 2-[(biphenyl-2-yloxy)methyl]oxirane
40 mg of 1-butyl-3-methylimidazolium bromide
5.9 g of 1,10-decanedithiol
Conditions: Reaction temperature 60° C. during dropwise addition, then 20 h reaction time at 60° C. then 20.5 h at 80° C.

A clear pale yellow product was obtained.

$^1$H NMR (CDCl$_3$, 400 MHz): δ (1H)=7.45 (d, 2H), 7.38 (t, 2H), 7.32 (m, 3H), 7.16 (t, 1H), 6.97 (d, 1H), 4.03 (d, 2H), 3.98 (m, 1H), 2.68 (dd, 1H, 2.55 (dd, 1H), 2.48 (t+s(b), 3H), 1.50 (p, 2H), 1.35 (m, 2H), 1.25 (s, 4H)

Example 9a

Ethane-1,2-diylbis({[3-(biphenyl-2-yloxy)-2-hydroxypropyl]sulphanyl}acetate)

Reactants: 14.3 g of 2-[(biphenyl-2-yloxy)methyl]oxirane
41 mg of 1-butyl-3-methylimidazolium bromide
6.0 g of glycol dimercaptoacetate
Conditions: Reaction temperature 60° C. during dropwise addition, then 25.5 h reaction time at 70° C.

A clear yellow product was obtained.

$^1$H NMR (CDCl$_3$, 400 MHz): δ (1H)=7.45 (d, 2H), 7.38 (t, 2H), 7.32 (m, 3H), 7.16 (t, 1H), 6.97 (d, 1H), 4.28 (s, 2H), 4.00 (m, 3H), 3.23 (s, 2H), 2.6-2.85 (m, 3H)

Example 10a

2-{[3-(Biphenyl-2-yloxy)-2-hydroxypropyl]sulphanyl}-3-{[3-(biphenyl-2-yloxy)-2-hydroxypropyl]sulphanyl}propan-1-ol Reactants: 38.2 g of 2-[(biphenyl-2-yloxy)methyl]oxirane
96 mg of triphenylphosphine
9.9 g of 2,3-disulphanylpropan-1-ol
Conditions: The initial charge was adjusted to 55° C. During the metered addition of the 2,3-disulphanylpropan-1-ol over 1 h, the reaction mixture heated up to 70° C. The reaction was exothermic (cooling!). This was followed by further stirring at 60° C. for 24 h.

A clear colourless high-viscosity product was obtained.

$^1$H NMR (CDCl$_3$, 400 MHz): δ (1H)=7.46 (d, 4H), 7.38 (t, 4H), 7.32 (m, 6H), 7.16 (t, 2H), 6.98 (dd, 2H), 3.93-4.02 (m, 6H), 3.57 (m, 1H), 3.40 (m, 1H), 2.88 (m, 1H), 2.53-2.75 (m, 6H), 2.50 (m, 1H), 2.28 (m, 1H).

Example 11a 3,3'-[Sulfanediylbis(benzene-4,1-diylsulphanediyl)]bis[1-(biphenyl-2-yloxy)propan-2-ol]

Reactants: 9.6 g of 2-[(biphenyl-2-yloxy)methyl]oxirane
13 mg of triphenylphosphine
6.0 g of 4,4'-sulphanediyldibenzenethiol
Conditions: Reaction temperature 60° C., reaction time at 30.5 h A clear glassy product was obtained.

$^1$H NMR (CDCl$_3$, 400 MHz): δ (1H)=7.45 (d, 2H), 7.38 (t, 2H), 7.30 (m, 3H), 7.18 (m, 4H), 7.07 (t, 1H), 6.92 (d, 1H), 4.04 (m, 2H), 3.96 (m, 1H), 3.09 (dd, 1H), 2.96 (dd, 1H), 2.39 (d, 1H, OH)

Precursor to Example 12a

2-[(Biphenyl-3-yloxy)methyl]oxirane 7.4 g of 3-phenylphenol, 52.7 g of 2-butanone and 21.5 g of potassium carbonate were initially charged to a three-neck flask equipped with KPG stirrer and stirring motor and also drier tube. After conditioning to 22° C. 23.8 g of epibromohydrin were added dropwise within about 2 hours, the temperature increased to 80° C. and then the mixture was stirred at about 75° C. for a further 45 hours. This was followed by filtration and removal of the solvent in a rotary evaporator to obtain a clear yellowish thinly liquid product.

$^1$H NMR (CDCl3, 400 MHz): δ (1H)=7.57 (d, 2H), 7.42 (t, 2H), 7.33 (m, 2H), 7.20 (d, 1H), 7.16 (t, 1.7 Hz, 1H), 6.90 (dd, 1H), 4.28 (dd, 1H), 4.02 (dd, 1H), 3.37 (m, 1H), 2.91 (dd, 1H), 2.77 (dd, 1H).

Example 12a 3,3'-(Propane-1,3-diyldisulphanediyl)bis[1-(biphenyl-3-yloxy)propan-2-ol]

Reactants: 7.5 g of product from the precursor to Example 12a 72 mg of 1-butyl-3-methylimidazolium bromide
1.3 g of 1,3-propanedithiol
Conditions: Reaction temperature 60° C. during the metered addition, then 80° C.; reaction time at 47 h A clear yellowish viscous product was obtained $^1$H NMR (CDCl$_3$, 400 MHz): δ (1H)=7.57 (d, 2H), 7.42 (t, 2H), 7.33 (t, 2H), 7.19 (d, 1H), 7.13 (t, 1.7 Hz, 1H), 6.88 (dd, 1H), 4.08-4.15 (m, 3H), 2.87 (dd, 1H), 2.75 (dd, 1H), including (b, 1H, OH), 2.69 (t, 2H), 1.90 (p, 1H)

General Method of Preparing the Inventive Di(Meth)Acrylates

Examples 1b-12b

The precursor (Example 1a-12a), dibutyltin dilaurate and 2,6-ditert-butyl-4-methylphenol were initially charged to a three-neck flask equipped with KPG stirrer and stirring motor, gas inlet and also drier tube. This was followed by heating at 60° C., air was slowly passed over and the 2-isocyanatoethyl acrylate was added dropwise in the course of about half an hour. Stirring was continued until the IR spectrum no longer showed any NCO band (2261 cm$^{-1}$).

Example 1b 6,13-Bis[(biphenyl-2-yloxy)methyl]-4,15,20-trioxo-5,14,19-trioxa-8,11-dithia-3,16-diazadocos-21-en-1-yl acrylate Reactants: 17.2 g of product from Example 1a
  8.5 g of 2-isocyanatoethyl acrylate
  13 mg of dibutyltin dilaurate
  3 mg of 2,6-ditert-butyl-4-methylphenol
Conditions: Reaction time 19 h at 60° C.
  A clear colourless high-viscosity product was obtained.
$n^{20}:_D$ 1.5904 (589 nm)

Example 2b 6,14-Bis[(biphenyl-2-yloxy)methyl]-4,16,21-trioxo-5,15,20-trioxa-8,12-dithia-3,17-diazatricos-22-en-1-yl acrylate Reactants: 17.6 g of product from Example 2a
  8.5 g of 2-isocyanatoethyl acrylate
  13 mg of dibutyltin dilaurate
  3 mg of 2,6-ditert-butyl-4-methylphenol
Conditions: Reaction time 3 h 50 minutes at 60° C., after 3 days' storage at room temperature NCO no longer detectable in IR.
  A clear colourless high-viscosity product was obtained.
$n^{20}:_D$ 1.5864 (589 nm)

Example 3b 6,15-Bis[(biphenyl-2-yloxy)methyl]-4,17,22-trioxo-5,16,21-trioxa-8,13-dithia-3,18-diazatetracos-23-en-1-yl acrylate Reactants: 21.0 g of product from Example 3a
  9.9 g of 2-isocyanatoethyl acrylate
  15 mg of dibutyltin dilaurate
  3 mg of 2,6-ditert-butyl-4-methylphenol
Conditions: Dropwise addition (exothermic!) in 15 minutes at 60° C., then reaction time of 18.7 h at 60° C.
  A clear, almost colourless, high-viscosity product was obtained.
$n^{20}:_D$ 1.5846 (589 nm)

Example 4b 6,13-Bis[(biphenyl-2-yloxy)methyl]-9,10-dimethyl-4,15,20-trioxo-5,14,19-trioxa-8,11-dithia-3,16-diazadocos-21-en-1-yl acrylate Reactants: 18.0 g of product from Example 4a
  8.5 g of 2-isocyanatoethyl acrylate
  13 mg of dibutyltin dilaurate
  3 mg of 2,6-ditert-butyl-4-methylphenol
Conditions: Dropwise addition (exothermic!) in 35 minutes at 60° C., then reaction time of 16 h at 60° C.
  A clear, almost colourless, high-viscosity product was obtained.
$n^{20}:_D$ 1.5840 (589 nm)

Example 5b 6,17-Bis[(biphenyl-2-yloxy)methyl]-4,19,24-trioxo-5,18,23-trioxa-8,15-dithia-3,20-diazahexacos-25-en-1-yl acrylate Reactants: 18.9 g of product from Example 5a
  8.5 g of 2-isocyanatoethyl acrylate
  14 mg of dibutyltin dilaurate
  3 mg of 2,6-ditert-butyl-4-methylphenol
Conditions: Dropwise addition (exothermic!) in 35 minutes at 60° C., then reaction time of 16 h at 60° C.
  A clear, almost colourless, high-viscosity product was obtained.
$n^{20}:_D$ 1.5801 (589 nm)

Example 6b 6,16-Bis[(biphenyl-2-yloxy)methyl]-4,18,23-trioxo-5,11,17,22-tetraoxa-8,14-dithia-3,19-diazapentacos-24-en-1-yl acrylate Reactants: 18.2 g of product from Example 6a
  8.5 g of 2-isocyanatoethyl acrylate
  13 mg of dibutyltin dilaurate
  5 mg of 2,6-ditert-butyl-4-methylphenol
Conditions: Reaction time 4 h
  A clear, pale yellow, high-viscosity product was obtained.
$n^{20}:_D$ 1.5814 (589 nm)

Example 7b 6,19-Bis[(biphenyl-2-yloxy)methyl]-4,21,26-trioxo-5,11,14,20,25-pentaoxa-8,17-dithia-3,22-diazaoctacos-27-en-1-yl acrylate Reactants: 19.5 g of product from Example 7a
  8.5 g of 2-isocyanatoethyl acrylate
  14 mg of dibutyltin dilaurate
  6 mg of 2,6-ditert-butyl-4-methylphenol
Conditions: Reaction time 4 h
  A clear, pale yellow, high-viscosity product was obtained.
$n^{20}:_D$ 1.5775 (589 nm)

Example 8b 6,21-Bis[(biphenyl-2-yloxy)methyl]-4,23,28-trioxo-5,22,27-trioxa-8,19-dithia-3,24-diazatriacont-29-en-1-yl acrylate Reactants: 20.2 g of product from Example 8a
  8.5 g of 2-isocyanatoethyl acrylate
  14 mg of dibutyltin dilaurate
  6 mg of 2,6-ditert-butyl-4-methylphenol
Conditions: Reaction time 24 h
  A clear, pale yellow, high-viscosity product was obtained.
$n^{20}:_D$ 1.5702 (589 nm)

Example 9b

8-[(Biphenyl-2-yloxy)methyl]-4,10,15-trioxo-3,9,14-trioxa-6-thia-11-azaheptadec-16-en-1-yl (5S)-5-[(biphenyl-2-yloxy)methyl]-7,12-dioxo-6,11-dioxa-3-thia-8-azatetradec-13-en-1-oate Reactants: 20.3 g of product from Example 9a
  8.5 g of 2-isocyanatoethyl acrylate
  14 mg of dibutyltin dilaurate 6 mg of 2,6-ditert-butyl-4-methylphenol
Conditions: Reaction time 18 h
A clear, yellow, high-viscosity product was obtained.
$n^{20}_D$ 1.5768 (589 nm)

Example 10b 6,13-Bis[(biphenyl-2-yloxy)methyl]-4,15,20-trioxo-10-[({[2-(phenylsulphanyl)phenyl]carbamoyl}oxy)methyl]-5,14,19-trioxa-8,11-dithia-3,16-diazadocos-21-en-1-yl acrylate Reactants: 4.8 g of product from Example 10a (triol)
1.8 g of 1-isocyanato-2-(phenylsulphanyl)benzene
2.3 g of 2-isocyanatoethyl acrylate
4 mg of dibutyltin dilaurate
1 mg of 2,6-ditert-butyl-4-methylphenol
20 g of chloroform
Conditions: First, triol, solvent, dibutyltin dilaurate and 2,6-ditert-butyl-4-methylphenol were initially charged at 30° C. and the 1-isocyanato-2-(phenylsulphanyl)benzene was added dropwise within 7 minutes. Stirring was continued for 2 h 45 min. Once the NCO signal had largely disappeared in the IR spectrum, the mixture was gradually heated to 60° C. within 70 minutes and the 2-isocyanatoethyl acrylate was added dropwise within 5 minutes. Stirring was continued for a further 14.5 h until the NCO signal was no longer detectable in the IR spectrum. Then, the solvent was removed in a rotary evaporator.
A clear high-viscosity product was obtained.
$n^{20}_D$ 1.6002 (589 nm)

Example 11b

Sulphanediylbis{benzene-4,1-diylsulphanediyl[3-(biphenyl-2-yloxy)propane-1,2-diyl]oxycarbonyliminoethan-2,1-diyl}bisacrylate Reactants: 14.6 g of product from Example 11a
5.6 g of 2-isocyanatoethyl acrylate
10 mg of dibutyltin dilaurate
2 mg of 2,6-ditert-butyl-4-methylphenol
Conditions: Reaction time 23 h.
A clear glassy product was obtained.
$n^{20}_D$ 1.6300 (589 nm)
$^1$H NMR (CDCl$_3$, 400 MHz): δ (1H)=7.47 (d, 2H), 7.23-7.37 (m, 6H), 7.18 (m, 4H, AA'BB'), 7.04 (t, 1H), 6.92 (d, 1H), 6.41 (d, 1H), 6.10 (dd, 1H), 5.83 (dd, 1H), 5.08 (p, 1H), 4.87 (t, 1H, NH), 4.10-4.23 (m, 4H), 3.43 (q, 2H), 3.12 (d, 2H)

Example 12b 6,14-Bis[(biphenyl-3-yloxy)methyl]-4,16,21-trioxo-5,15,20-trioxa-8,12-dithia-3,17-diazatricos-22-en-1-yl acrylate Reactants: 9.3 g of product from Example 12a
4.6 g of 2-isocyanatoethyl acrylate
7 mg of dibutyltin dilaurate
1 mg of 2,6-ditert-butyl-4-methylphenol
Conditions: Reaction time 1 h 50 min.
A clear yellowish high-viscosity product was obtained.
$n^{20}_D$ 1.5908 (589 nm)

Comparative Example 1

Phosphorothioyltris(oxybenzene-4,1-diylcarbamoyloxyethane-2,1-diyl)trisacrylate [1072455-04-9]

In a 500 mL round-bottom flask, 0.1 g of 2,6-ditert-butyl-4-methylphenol, 0.05 g of dibutyltin dilaurate and also and 213.07 g of a 27% solution of tris(p-isocyanatophenyl)thiophosphate in ethyl acetate were initially charged and heated to 60° C. This was followed by the dropwise addition of 42.37 g of 2-hydroxyethyl acrylate and further maintenance of the mixture at 60° C. until the isocyanate content had dropped to below 0.1%. This was followed by cooling and complete removal of the ethyl acetate in vacuo. The product was obtained as a partly crystalline solid. The product obtained had an $n^D{}_{20}$=1.5430 (589 nm).

Comparative Example 2

Benzene-1,3-diylbis[oxy-3-(biphenyl-4-yloxy)propane-1,2-diyl]bisacrylate

Comparative Example 2—1st Stage

Conversion of 2,2'-[benzene-1,3-diylbis(oxymethylene)]dioxirane (resorcinol diglycidyl ether) to 1,1'-[benzene-1,3-diylbis(oxy)]bis[3-(biphenyl-4-yloxy)propan-2-ol]

Proceeding analogously to Example 1 [0192] in EP 1 627 867 A1 (conversion of formula 10-1 to formula 5-1) 18.7 g of 4-phenylphenol and 1.3 mg of triphenylphosphine were melted at 160° C. Then, 11.8 g of resorcinol diglycidyl ether (commercially available as Denacol LSC 201 from Nagase & Co., Ltd. Japan) were added, followed by stirring for ten hours. Then, a further 3.9 mg of triphenylphosphine were added, followed by stirring at 170° C. for a further 24 h. After cooling, the product was recrystallized in butyl acetate.
$^1$H NMR conforms to: $^1$H NMR (400 MHz, CDCl3): 2.54 (d, 2H, OH), 4.10-4.22 (m, 8H, OCH2CH), 4.35-4.45 (m, 2H, CH2CHOH—CH2), 6.5-6.6 (m, 3H), 7.0 (AA'BB', 4H), 7.20 (t, 1H), 7.30 (t, 2H), 7.40 (t, 4H), 7.50-7.55 (m, 8H)

Comparative Example 2—2nd Stage

Conversion of 1st Stage to benzene-1,3-diylbis[oxy-3-(biphenyl-4-yloxy)propane-1,2-diyl]bis(3-chloropropanoate)

Proceeding analogously to Example 2 [0195] in EP 1 627 867 A1 (conversion of formula 5-1 to formula 6-1) 2.9 g of Comparative Example 2—1st stage in 50 g of butyl acetate were heated at 68° C. This was followed by addition of 1.8 g of triethylamine and heating to 85° C. to obtain a clear solution. Then, 2.3 g of 3-chloropropionic acid chloride were added dropwise during half an hour. In the process, the solution heated up to 126° C. The temperature was adjusted to 112° C. before stirring for a further four hours and cooling. The cooled product was poured into 200 ml of ice-water followed by extraction with 150 ml of toluene. After phase separation, the toluene phase was washed with 100 ml of 3% NaHCO$_3$ solution. Toluene was distilled off in a rotary evaporator at 40° C. to leave the crude product. The $^1$H NMR conformed, also showed amounts of the desired end product (elimination product).

Comparative Example 2—3rd Stage

Conversion of 2nd stage to benzene-1,3-diylbis[oxy-3-(biphenyl-4-yloxy)propane-1,2-diyl]bisacrylate In accordance with Example 1 [0128] in EP 1 627 867 A1 (elimination to formula 1-1) 2.77 g of the crude product were dissolved in 50 g of acetone and temperature controlled to 5° C. Then, 1.25 g of triethylamine were added during 30 minutes and the solution was maintained at 5° C. for 70 hours. After warming to 25° C. 100 g of toluene and 100 g of water were added. The phases were separated and the toluene phase was washed with 10 ml of 5% hydrochloric acid. This was followed by eight further washes with 50 ml of water until the wash water was neutral. 0.2 mg of p-methoxyphenol were added and the product was substantially freed of the solvent at 40° C. in a rotary evaporator. $^1$H NMR (400 MHz, CDCl3): 4.10-4.40 (m, 8H), 5.5 (m, 2H, CH), 5.85 (d, 2H, acrylate), 6.18 (dd, 2H, acrylate), 6.45 (d, 2H, acrylate), 6.50-6.60 (m, 3H), 6.98 (AA'BB', 4H), 7.20 (t, 1H), 7.30 (t, 2H), 7.38 (t, 4H), 7.50 (m, 8H).

Polyol Component:

In a 1 L flask, 0.18 g of Addocat® SO, 374.8 g of ε-caprolactone and 374.8 g of a difunctional polytetrahydrofuran polyether polyol (equivalent weight 650 g/mol of OH) were initially charged and heated to 120° C. and maintained at 120° C. until the solids content (proportion of nonvolatile constituents) was 99.5% by weight or higher. This was followed by cooling to obtain the product as a waxy solid.

Urethane acrylate 1: 2-({[3-(Methylsulphanyl)phenyl]carbamoyl}oxy)ethyl prop-2-enoate In a 100 mL round-bottom flask, 0.02 g of 2,6-ditert-butyl-4-methylphenol, 0.01 g of Desmorapid Z, 11.7 g of 3-(methylthio)phenyl isocyanate were initially charged and heated to 60° C. This was followed by the dropwise addition of 8.2 g of 2-hydroxyethyl acrylate and the mixture was maintained at 60° C. until the isocyanate content dropped to below 0.1%. This was followed by cooling. The product was obtained as a colourless liquid.

Fluorinated urethane: Bis(2,2,3,3,4,4,5,5,6,6,7,7-dodecafluoroheptyl)(2,2,4-trimethylhexane-1,6-diyl)biscarbamate In a 6 L round-bottom flask, 0.50 g of Desmorapid Z and 1200 g of trimethylhexamethylene diisocyanate were initially charged and heated to 80° C. This was followed by the dropwise addition of 3798 g of 1H,1H,7H-perfluoroheptan-1-ol and the mixture was maintained at 80° C. until the isocyanate content dropped to below 0.1%. This was followed by cooling. The product was obtained as a colourless oil.

Preparing the Inventive and Noninventive Media (Coupons)

Examples 13 to 24 and Comparative Examples 3 and 4

2.940 g of the polyol component described above were mixed with 2.000 g of the respective acrylate (Examples 1 to 12, Comparative Example 1), 2.000 g of the above-described urethane acrylate 1, 2.000 g of the above-described fluorinated urethane, 0.15 g of CGI 909, 15 mg of crystal violet, 15 mg of Irgacure 250, 15 mg of glass beads sized 9.18 μm and 0.517 g g of N-ethylpyrolidone at 60° C. to obtain a clear (slightly cloudy in some places) solution. This was followed by cooling to 30° C., adding 545 mg of Desmodur® N 3900 and renewed mixing. Finally, 6 mg of Fomrez UL 28 were added followed again by brief mixing. The liquid mass obtained was then applied to a glass plate (from Corning, N.Y. 14831, USA, micro slide plane: thickness 0.96-1.06 mm, 75 mm×50 mm, type: 2947–75×50) and covered there with a second glass plate. This test specimen was stored at room temperature for 12 hours, curing in the process. Then, the media were packed impervious to light.

Determining the Physical Data of Inventive and Noninventive Media

The holographic properties DE and Δn were measured using the "methods of measurement" described above.

Haze was likewise measured using the method described above in the "methods of measurement", although, before measurement, the respective medium was initially bleached at room temperature and ambient light for about 15-30 minutes until the colour was visually no longer discernible.

The results of the measurements are shown in the table which follows:

| Example | Acrylate | R of inventive di(meth)acrylate | Number of atoms in R | | | | | Refractive index (at 589 nm) | Haze [%] | Refractive index contrast (Δn) at 15.9 [mJ/cm2] |
|---|---|---|---|---|---|---|---|---|---|---|
| | | | Carbon | Oxygen | Sulphur | Nitrogen | Sum total | | | |
| 13 | 7b | HS—CH2—CH2—O—CH2—CH2—O—CH2—CH2—SH | 6 | 2 | 2 | — | 10 | 1.5775 | 0.9 | 0.0290 |
| 14 | 4b | HS—CH2CH3—CH2CH3—SH | 4 | — | 2 | — | 6 | 1.5840 | 1.0 | 0.0315 |
| 15 | 6b | HS—CH2—CH2—O—CH2—CH2—SH | 4 | 1 | 2 | — | 7 | 1.5814 | 1.4 | 0.0292 |
| 16 | 10b | HS—CH2—CHR1—SH, R1 = CH2O—CO—NH—PhSPh | 16 | 2 | 3 | 1 | 22 | 1.6002 | 3.5 | 0.0280 |
| 17 | 8b | HS—[CH2]10—SH | 10 | — | 2 | — | 12 | 1.5702 | 33.4 | 0.0306 |
| 18 | 11b | HS—Ph—S—Ph—SH | 12 | — | 3 | — | 15 | 1.6300 | 36.0 | 0.0260 |
| 19 | 5b | HS—CH2—CH2—CH2—CH2—CH2—CH2—SH | 6 | — | 2 | — | 8 | 1.5801 | 36.2 | 0.0295 |
| 20 | 3b | HS—CH2—CH2—CH2—CH2—SH | 4 | — | 2 | — | 6 | 1.5846 | 39.5 | 0.0252 |
| 21 | 9b | HS—CH2—CO—O—CH2—CH2—O—CO—CH2—SH | 6 | 4 | 2 | — | 12 | 1.5768 | 40.7 | 0.0322 |
| 22 | 12b | HS—CH2—CH2—CH2—SH* | 3 | — | 2 | — | 5 | 1.5908 | 41.3 | 0.0345 |
| 23 | 2b | HS—CH2—CH2—CH2—SH | 3 | — | 2 | — | 5 | 1.5864 | 55.6 | 0.0295 |
| 24 | 1b | HS—CH2—CH2—SH | 2 | — | 2 | — | 4 | 1.5904 | 61.7 | 0.0273 |

2-[(biphenyl-2-yloxy)methyl]oxirane was used unless otherwise stated

| | | | Number of atoms in R | | | | Refractive index (at 589 nm) | Haze [%] | Refractive index contrast (Δn) at 15.9 [mJ/cm2] |
|---|---|---|---|---|---|---|---|---|---|
| Example | Acrylate | R of inventive di(meth)acrylate | Carbon | Oxygen | Sulphur | Nitrogen | Sum total | | | |
| Comparative Example 3 | Comparative Example 1 | Phosphorothioyltris(oxybenzene-4,1-diylcarbamoyloxyethane-2,1-diyl) trisacrylate | | | | | | 1.5430 | 54.9 | 0.0240 |
| Comparative Example 4 | Comparative Example 2 | Benzene-1,3-diylbis[oxy-3-(biphenyl-4-yloxy)propane-1,2-diyl] bisacrylate | | | | | | 1.6025* | 45.0 | 0.0240 |

*2-[(biphenyl-3-yloxy)-methyl]oxirane was used
Ph = phenyl or phenylene

*Comparative Example 2 is a crystalline compound. Therefore, the refractive index was determined after melting the sample and transferring it speedily into the refractometer. The measured value was determined shortly before the recrystallizing in the refractometer.

As the table reveals, the media which contain an inventive compound as per formula (I) as writing monomer show a distinctly higher refractive index contrast Δn than the medium of Comparative Example 3, which in turn contains a writing monomer known from WO 2008/125199. This also holds for the medium of Comparative Example 4, wherein a writing monomer known from EP 1 627 867 A1 was used. In addition, media obtained using the inventive compounds, however, also show a particularly low haze, which is advantageous for optical articles in general and for transmission holograms in particular.

The invention claimed is:

1. A photopolymer formulation comprising at least a polyisocyanate component a), a polyol component b), a photoinitiator c) and a writing monomer d), wherein at least one compound of formula (I)

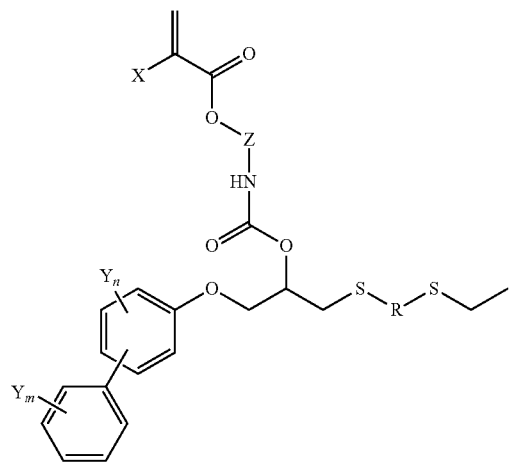

Formula (I)

-continued

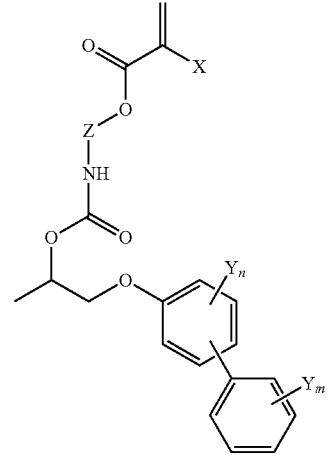

where:
X is $CH_3$ or hydrogen,
Z is a linear or branched C2 to C4 alkyl radical,
R is a linear or branched, optionally heteroatom-substituted aliphatic, aromatic or araliphatic radical,
Y in each occurrence is independently hydrogen, methyl, ethyl, propyl, n-butyl, tert-butyl, chlorine, bromine, iodine, methylthio, phenyl or phenylthio,
n is from 0 to 4, and
m is from 0 to 5,
is present as writing monomer d),
wherein said photopolymer formulation further comprises a plasticizer according to formula (II)

$$\left[ R_1 - O - \overset{O}{\underset{}{C}} - \underset{R_2}{\overset{R_3}{N}} \right]_p \quad (II)$$

where p is >1 and <8 and $R^1$, $R^2$, $R^3$, independently of one another are hydrogen or independently linear, branched, cyclic or heterocyclic organic radicals which are unsubstituted or optionally heteroatom-substituted, and wherein at least one of the radicals $R^1$, $R^2$, $R^3$ is substituted with at least a fluorine atom.

2. The photopolymer formulation according to claim 1, wherein at least one monofunctional urethane(meth)acrylate is present as further writing monomer.

3. The photopolymer formulation according to claim 1, wherein said polyol component is a difunctional polyether, polyester or a polyether-polyester block copolyester with primary OH functions.

4. The photopolymer formulation according to claim 1, wherein said polyisocyanate component is an aliphatic polyisocyanate or a prepolymer with primary NCO groups.

5. The photopolymer formulation according to claim 1, wherein said photoinitiator comprises a combination of dyes having absorption spectra covering at least partly the spectral region from 400 to 800 nm, with at least one suitable coinitiator.

6. The photopolymer formulation according to claim 1, which is capable of being used for producing holographic media optionally for recording in-line, off-axis, full-aperture, transfer, white light, transmission, Denisyuk, off-axis reflection or edge-lit holograms and/or holographic stereograms.

* * * * *